US012594366B2

(12) United States Patent
Fuertinger et al.

(10) Patent No.: US 12,594,366 B2
(45) Date of Patent: Apr. 7, 2026

(54) TECHNIQUES FOR DIALYSIS BASED ON RELATIVE BLOOD VOLUME

(71) Applicants: Fresenius Medical Care Holdings, Inc., Waltham, MA (US); Fresenius Medical Care Deutschland GmbH, Bad Homburg (DE)

(72) Inventors: Doris H. Fuertinger, Long Island City, NY (US); Peter Kotanko, New York, NY (US); Sabrina Rogg, Bad Homburg (DE)

(73) Assignees: Fresenius Medical Care Holdings, Inc., Waltham, MA (US); Fresenius Medical Care Deutschland GmbH, Bad Homburg (DE)

( * ) Notice: Subject to any disclaimer, the term of this patent is extended or adjusted under 35 U.S.C. 154(b) by 868 days.

(21) Appl. No.: 16/574,874

(22) Filed: Sep. 18, 2019

(65) Prior Publication Data

US 2020/0086026 A1 Mar. 19, 2020

Related U.S. Application Data

(60) Provisional application No. 62/733,485, filed on Sep. 19, 2018.

(51) Int. Cl.
*A61M 1/16* (2006.01)
*A61M 1/30* (2006.01)
*A61M 1/34* (2006.01)

(52) U.S. Cl.
CPC ........ *A61M 1/1611* (2014.02); *A61M 1/1613* (2014.02); *A61M 1/308* (2014.02); *A61M 1/3441* (2013.01); *A61M 2230/207* (2013.01)

(58) Field of Classification Search
CPC .. A61M 1/1611; A61M 1/1613; A61M 1/308; A61M 1/3441; A61M 2230/207;
(Continued)

(56) References Cited

U.S. PATENT DOCUMENTS 11,253,638 B2 2/2022 Steger et al.
2003/0152482 A1* 8/2003 O'Mahony ......... A61M 1/3656
604/4.01
(Continued)

FOREIGN PATENT DOCUMENTS

CN 107224624 A 10/2017
EP 2469431 6/2012
(Continued)

OTHER PUBLICATIONS

Flythe et al. Kidney International (2011) 79, 250-257 (Year: 2011).*
(Continued)

*Primary Examiner* — Krishnan S Menon
(74) *Attorney, Agent, or Firm* — KDW Firm PLLC

(57) ABSTRACT

Systems, methods, and/or apparatuses may be operative to perform a dialysis process using RBV-based UF control. Embodiments may include methods operative to receive RBV target information comprising population-based dialysis data of real patient outcomes of a patient population associated with the patient, determine an RBV value of a patient during the dialysis process, and determine UF information to control a UF pump of the dialysis device to maintain the RBV value within a target RBV range defined by the RBV target information. Other embodiments are described.

12 Claims, 39 Drawing Sheets

(58) Field of Classification Search

CPC .. A61M 1/3448; A61M 60/113; A61M 60/37; G16H 40/63; G16H 20/40

See application file for complete search history.

(56) References Cited

U.S. PATENT DOCUMENTS

| 2011/0036773 A1 | 2/2011 | Moissl et al. |
| 2013/0041684 A1 | 2/2013 | Kotanko |
| 2013/0134077 A1 | 5/2013 | Wieskotten |
| 2013/0261529 A1 | 10/2013 | O'Mahony |
| 2013/0274644 A1 | 10/2013 | Hertz |
| 2013/0317850 A1 | 11/2013 | Bene |
| 2015/0045633 A1 | 2/2015 | Berkow |
| 2015/0065826 A1 | 3/2015 | Mulligan |
| 2017/0228509 A1 | 8/2017 | Ahrens |
| 2017/0239409 A1* | 8/2017 | De los Reyes, V .......................... A61B 5/02028 |
| 2019/0200921 A1* | 7/2019 | Barrett ................ A61M 1/3403 |

FOREIGN PATENT DOCUMENTS

| JP | S61203972 A | 9/1986 |
| JP | 2001000540 A | 1/2001 |
| JP | 2010063644 A | 3/2010 |
| WO | 2015179401 A1 | 11/2015 |

OTHER PUBLICATIONS

Control System Designs—PID Control by Astrom et al., Department of Automatic Control LTH, Lund University, 2006 (Year: 2006).*

Andrulli S, et al., "The role of blood volume reduction in the genesis of intradialytic hypotension", Am J Kidney Dis 40(6):1244-1254 (2002).

Flythe, JE., et al., "Association of mortality risk with various definitions of intradialytic hypotensio," J Am Soc Nephrol 26:724-734 (2015).

Malhotra R., et al., "Relationship of neutrophil-to-lymphocyte ratio and serum albumin levels with C-reactive protein in hemodialysis patients: results from 2 international cohort studies," Nephron 1(30):263-270 (2015).

Flythe JE, et al., "Associations of posthemodialysis weights above and below target weight with all-cause and cardiovascular mortality", Clin J Am Soc Nephrol 10:808-816 (2015).

Chazot C, et al., "Importance of normohydration for the long-term survival of haemodialysis patients", Nephrol Dial Transplant 27:2404-2410 (2012).

Daugirdas JT., "Pathophysiology of dialysis hypotension: an update", Am J Kidney Dis 38(4):S11-S17 (2001). abstract.

De los Reyes V AA, et al., "A physiologically based model of vascular refilling during ultrafiltration in hemodialysis", J Theor Biol 390:146-155 (2016). abstract.

Paguio VME, et al., "A model of vascular refilling with inflammation," Math Biosci 303:101-114 (2018). abstract.

Lopot F, et al., "Use of continuous blood vol. monitoring to detect inadequately high dry weight," Int J Artif Organs 19:411-414 (1996).abstract.

Beige J, et al., "Computational analysis of blood vol. curves and risk of intradialytic morbid events in hemodialysis." Kidney Int 58:1805-1809 (2000).

Howard, AD et al., "Assessing the value of blood vol. monitoring to improve outcomes. A comparative observational study", Nephrol News Issues 12(5):24-26 (1998) abstract.

Agarwal, R., "Hypervolemia is associated with increased mortality among hemodialysis patients", Hypertension 56:512-517 (2010).

Agarwal, R, et al., "Diagnostic utility of blood vol. monitoring in hemodialysis patients," AmJ Kidney Dis 51(2): 242-254 (2008) abstract.

Krepel, HP., et al., "Variability of relative blood vol. during haemodialysis",.Nephrol Dial Transplant 15:673-679 (2000).

Booth, J., et al., "Do changes in relative blood vol. monitoring correlate to hemodialysis-associated hypotension?" Nephron Clin Pract 117:c179-c183 (2011).

Steuer, R.R., et al., " Enhanced fluid removal guided by blood vol. monitoring during chronic hemodialysis," Artif Organs 22(8):627-632 (1998). abstract.

Canaud, B., et al., "Clinical practices and outcomes in elderly hemodialysis patients: results from the Dialysis Outcomes and Practice Patterns Study (DOPPS)," Clin J Am Soc Nephrol 6:1651-1662 ( 2011).

Rottembourg, J., et al., "Evolution of residual renal function in patients undergoing maintenance haemodialysis or continuous ambulatory peritoneal dialysis," Proc Eur Dial Transplant Assoc 19:397-403 (1983). abstract.

Gil, H-W, et al. "Efficacy of Hemocontrol Biofeedback System in Intradialytic Hypotension-Prone Hemodialysis Patients," Journal of Korean Medical Science, 29(6):805-10 (2014).

Levin, N.W., et al. "Hemodynamic response to fluid removal during hemodialysis: categorization of causes of intradialytic hypotension." Nephrology Dial Transplant 33:1643-1649 (2018).

Sands, J.J., et al., "Intradialytic hypotension: frequency, sources of variation and correlation with clinical outcome," Hemodialysis international International Symposium on Home Hemodialysis, 18(2):415-22 (2014). abstract.

Preciado ,P., et al., "All-cause mortality in relation to changes in relative blood volume during hemodialysis," Nephrology Dial Transplant 34:1401-1408 (2018).

Covic, A., & Onofriescu, M., "Time to Improve Fluid Management in Hemodialysis: Should We Abandon Clinical Assessment and Routinely Use Bioimpedance?" Clinical Journal of the American Society of Nephrology, 8(9):1474-5 (2013).

Van der Sande, F.M, et al., "Novel Insights into the Pathogenesis and Prevention of Intradialytic Hypotension," Blood Purification, 45(1-3):230-5 (2018).

Orofino, L., et al. "Epidemiology of Symptomatic Hypotension in Hemodialysis: Is Cool Dialysate Beneficial for All Patients?", American Journal of Nephrology 10(3):177-80 (1990). abstract.

Burton, J.O., et al., "Hemodialysis-Induced Left Ventricular Dysfunction is Associated with an Increase in Ventricular Arrhythmias," Renal Failure 30(7):701-9 (2008).

Burton, J.O., et al., "Hemodialysis-Induced Cardiac Injury: Determinants and Associated Outcomes," Clinical Journal of Am Soc Nephrol 4(5):914-20 (2009).

Shoji, T., et al., "Hemodialysis-associated hypotension as an independent risk factor for two-year mortality in hemodialysis patients," Kidney International 66:1212-20 (2004).

Keane, D.F., et al., "Time to Reconsider the Role of Relative Blood Volume Monitoring for Fluid Management in Hemodialysis," American Society for Artificial Internal Organs 64(6):812-818 (2018).

Dasselaar J.J., et al., "Relative blood vol. measurements during hemodialysis: Comparisons between three noninvasive devices," Hemodialysis International Symposium on Home Hemodialysis. 11(4):448-5 (2007). abstract.

Basile C., et al. "Efficacy and Safety of Haemodialysis Treatment with the Hemocontrol Biofeedback System: A Prospective Medium-Term Study", Nephrol Dial Transplant 16(2):328-334 (2001).

Begin V., et al., "Biofeedback regulation of ultrafiltration and dialysate conductivity for the prevention of hypotension during hemodialysis", American Society for Artificial Internal Organs, 48(3):312-5. ( May-Jun. 2002).

Ronco C., et al., "Impact of biofeedback-induced cardiovascular stability on hemodialysis tolerance and efficiency." Kidney international, 58(2):800-808 (2000).

Santoro A., et al., "Blood vol. controlled hemodialysis in hypotension-prone patients: A randomized, multicenter controlled trial." Kidney international, 62(3):1034-45 (2002).

Santoro A., et al. "Blood vol. Regulation During Hemodialysis." American Journal of Kidney Diseases, 32(5):739-48 (1998). abstract.

Reddan, D.N., et al. "Intradialytic Blood vol. Monitoring in Ambulatory Hemodialysis Patients: A Randomized Trial", Journal of the American Society of Nephrology, 16(7):2162-9 (2005).

(56) References Cited

OTHER PUBLICATIONS

Santoro A., et al., "Automatic Control of Blood vol. Trends During Hemodialysis", American Society for Artificial Internal Organs, 40(3):M419-22, (1994).

Leung K.C.W., et al., "Randomized Crossover Trial of Blood Volume Monitoring-Guided Ultrafiltration Biofeedback to Reduce Intradialytic Hypotensive Episodes with Hemodialysis", Clinical Journal of the American Society of Nephrology, 12(11):1831-40 (2017).

Deziel C., et al., "Impact of Hemocontrol on Hypertension, Nursing Interventions, and Quality of Life: A Randomized, Controlled Trial", Clinical Journal of the American Society of Nephrology, 2(4):661-8 (2007).

Gabrielli D., et al., "Improved intradialytic stability during haemodialysis with blood volume-controlled ultrafiltration", Journal of Nephrology, 22(2):232-40 (2009). abstract.

Locatelli F., et al. "Effect of a plasma sodium biofeedback system applied to HFR on the intradialytic cardiovascular stability. Results from a randomized controlled study." Nephrology, dialysis, transplantation: official publication of the European Dialysis and Transplant Association—European Renal Association, 27(10):3935-42 (2012).

Mancini E., et al., "Prevention of dialysis hypotension episodes using fuzzy logic control system." Nephrol Dial Transplant 22(5):1420-7 (2007).

Nesrallah G.E., et al."Can Extracellular Fluid vol. Expansion in Hemodialysis Patients be Safely Reduced Using the Hemocontrol Biofeedback Algorithm? A Randomized Trial", American Society for Artificial Internal Organs, 54(3):270-4 (2008).

Selby N.M., et al., "Occurrence of Regional Left Ventricular Dysfunction in Patients Undergoing Standard and Biofeedback Dialysis", American Journal of Kidney Diseases, 47(5):830-41(2006) abstract.

McIntyre C.W., et al., "Biofeedback controlled hemodialysis (BF-HD) reduces symptoms and increases both hemodynamic tolerability and dialysis adequacy in non-hypotension prone stable patients", Clinical Nephrology, 60(2):105-12 (2003). abstract.

Fishbane, S., et al., "Changes to the End-Stage Renal Disease Quality Incentive Program", Kidney International, 81:1167-1171 (2012).

Salman, L., et al., "Interventional Nephrology: Physical Examination as a Tool for Surveillance for the Hemodialysis Arteriovenous Access", Clin J Am Soc Nephrol 8:1220-1227 (2013).

Haussecker, H., & Fleet, D.J., "Estimating Optical Flow with Physical Models of Brightness Variation", IEEE Conference on Computer Vision and Pattern Recognition, 2:760-767 (2000).

Campos, R.P., et al., "Accuracy of Physical Examination and Intra-Access Pressure in the Detection of Stenosis in Hemodialysis Arteriovenous Fistula", Semin Dial, 21(3):269-273 (2008).

Wu, H-Y, et al., "Eulerian Video Magnification for Revealing Subtle Changes in the World", ACM Transactions on Graphics, 31(4)Article 65:1-8 (2012).

Nakajima, K., et al., " Detection of apparent skin motion using optical flow analysis: Blood pulsation signal obtained from optical flow sequence", Rev. Sci. Instrum, 68(2):1331-1336 (1997). abstract.

Zhu, F., et al., "Estimation of arterio-venous access blood flow in hemodialysis patients using video image processing technique," 2016 38th Annual International Conference of the IEEE Engineering in Medicine and Biology Society (EMBC), Orlando, FL, 2016, pp. 207-210. abstract.

Zhu, F., et al., "Assessment of Fistula Flow Using Smartphone Video Analysis", ASN abstract 2019 (Submission).

International Search Report and Written Opinion for International application No. PCT/US2019/051715, mailed on Jan. 2, 2020, 14 pages.

Zhu, F., et al., "Continuous Measurement of Calf Resistivity in Hemodialysis Patients using Bioimpedance Analysis," 2006 International Conference of the IEEE Engineering in Medicine and Biology Society, New York, NY, 2006, pp. 5126-5128. abstract.

Dou, Y., et al., "Assessment of extracellular fluid vol. and fluid status in hemodialysis patients: current status and technical advances", Semin Dial 25(4):377-387 (2012) abstract.

Kalantar-Zadeh, K., et al., "Fluid retention is associated with cardiovascular mortality in patients undergoing long-term hemodialysis", Circulation 119: 671-679, (2009).

Wizemann, V., et al., "The mortality risk of overhydration in haemodialysis patients", Nephrol Dial Transplant 24:1574-1579 (2009).

Xu, Y., et al., "Hypertension, fluid overload and micro inflammation are associated with left ventricular hypertrophy in maintenance hemodialysis patients", Renal Failure 35(9):1204-1209 (2013).

Dekker, MJE, et al., "Impact of fluid status and inflammation and their interaction on survival: a study in an international hemodialysis patient cohort," Kidney Int 91:1214-1223 (2017).

Daugirdas, J.T., "Dialysis hypotension: a hemodynamic analysis", Kidney Int 39(2):233-246 (1991).

Van der Sande, F.M., et al., "Intradialytic hypotension—new concepts on an old problem", Nephrol Dial Transplant 15:1746-1748 (2000).

McIntyre, C.W., et al., "Hemodialysis-induced cardiac dysfunction is associated with an acute reduction in global and segmental myocardial blood flow," Clin J Am Soc Nephrol 3:19-26 (2008).

Buchanan, C, et al., "Intradialytic cardiac magnetic resonance imaging to assess cardiovascular responses in a short-term trial of hemodiafiltration and hemodialysis", J Am Soc Nephrol 28:1269-1277 (2017).

Barth, C., et al. Characteristics of hypotension-prone haemodialysis patients: is there a critical relative blood volume? Nephrol Dial Transplant 18:1353-1360 (2003).

Steuer, R.R., et al., "Hematocrit as an indicator of blood vol. and predictor of intradialytic morbid events", ASAIO J 40:M691-M696 (1994).

Steuer, R.R., et al., "Reducing symptoms during hemodialysis by continuously monitoring the hematocrit", Am J Kidney Dis 27(4):525-532 (1996). abstract.

Misra, M., et al., "Effect of cause and time of dropout on the residual GFR: a comparative analysis of the decline of GFR on dialysis", Kidney Int 59:754-763 (2001).

* cited by examiner

402

_600_

_FIG. 6A_

_600_

_FIG. 6B_

_800_

Figure 9:
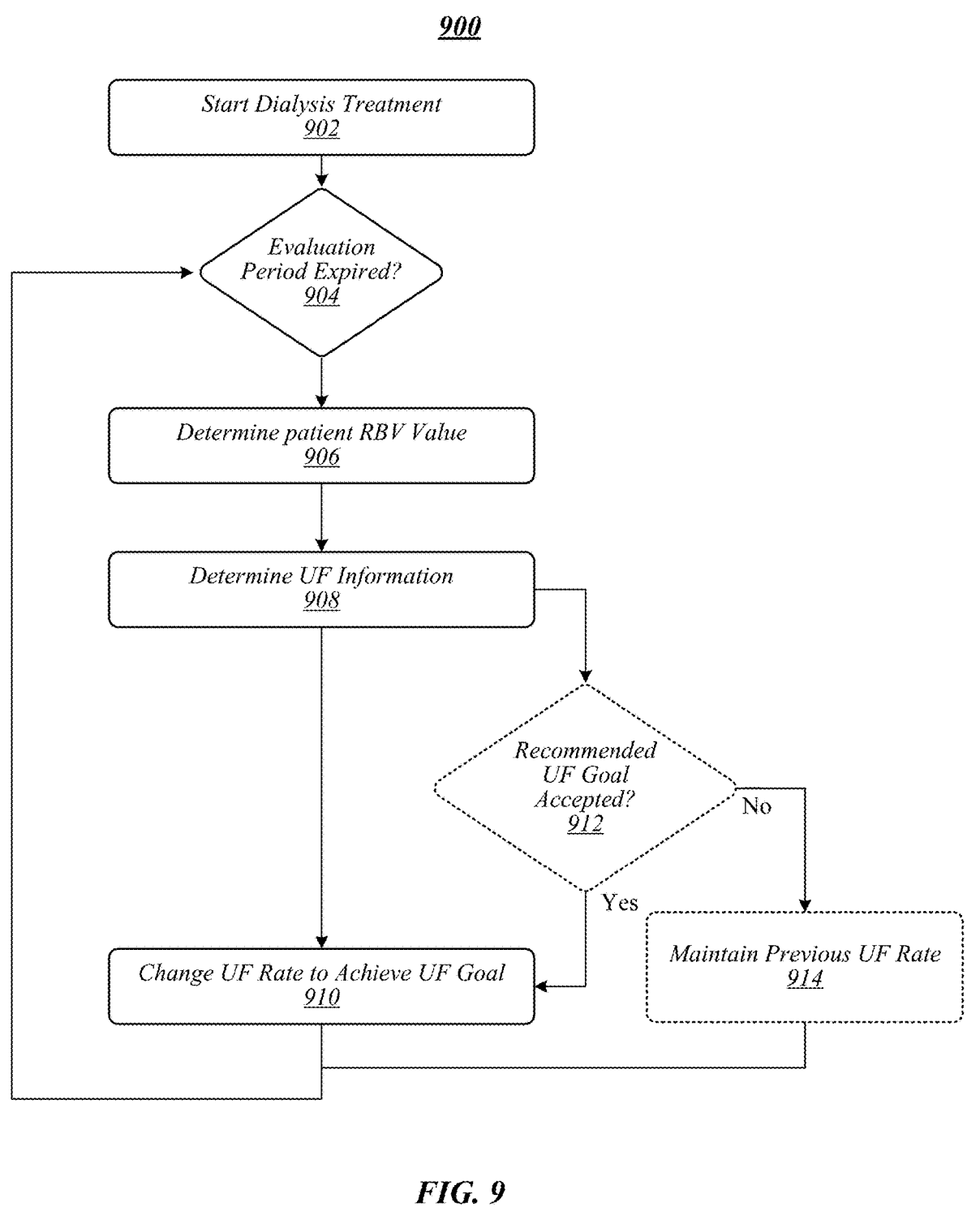

*900*

Start Dialysis Treatment
*902*

Evaluation
Period Expired?
*904*

Determine patient RBV Value
*906*

Determine UF Information
*908*

Recommended
UF Goal
Accepted?
*912*

No

Yes

Maintain Previous UF Rate
*914*

Change UF Rate to Achieve UF Goal
*910*

| Favorable RBV range | 1 h, 93-96% | 2 h, 89-94% | 3 h, 86-92% |
|---|---|---|---|
| Above, n (%) | 550 (65.3) | 551 (65.4) | 554 (65.8) |
| Within, n (%) | 270 (32.1) | 273 (32.5) | 273 (32.5) |
| Below, n (%) | 22 (2.6) | 18 (2.1) | 15 (1.8) |

| Time (favorable RSV range) | Crude model[a] | | Minimally adjusted model[b] | | Fully adjusted model[c] | |
|---|---|---|---|---|---|---|
| | HR (95% CI) | P-value | HR (95% CI) | P-value | HR (95% CI) | P-value |
| First tour (93-96%) | 0.57 (0.43-0.77) | 0.0002 | 0.64 (0.48-0.87) | 0.003 | 0.58 (0.43-0.79) | 0.0005 |
| Second tour (89-93%) | 0.52 (0.38-0.69) | <0.001 | 0.63 (0.46-0.85) | 0.002 | 0.54 (0.39-0.75) | <0.001 |
| Third tour (86-92%) | 0.43 (0.31-0.58) | <0.001 | 0.57 (0.42-0.79) | [illegible] | 0.46 (0.33-0.65) | <0.001 |

[a] Unadjusted model

[b] Adjusted for age, sex, COPD and CHF

[c] Adjusted for age, sex, race, COPD, CHF, diabetes, albumin, hemoglobin, NLR, predicted SBP and DBP.

| Subgroup (n) | RBV (%) 1 h | RBV (%) 2 h | RBV (%) 3 h |
|---|---|---|---|
| All patients (842) | 93–96 | 89–94 | 86–92 |
| Age (years) | | | |
| ≤61 (421) | 95–96 | 90–93 | 86–90 |
| >61 (421) | 93–96 | 90–94 | 88–92 |
| Race | | | |
| White (426) | 94–96 | 91–94 | 87–92 |
| Nonwhite (416) | 94–96 | 90–93 | 86–91 |
| Sex | | | |
| Male (523) | 94–96 | 90–94 | 87–92 |
| Female (319) | 93–96 | 90–93 | 86–91 |
| Predialysis SBP (mmHg) | | | |
| ≤ 130 (180) | 94.8–95.2 | 90–94 | 87–92 |
| >130 (662) | 94–96 | 90–93 | 86–91 |
| Interdialytic weight gain (kg) | | | |
| ≤ 2.3 (421) | n.s. | n.s. | 90–92 |
| > 2.3 (421) | 93–96 | 89–93 | 85–91 | n.s., not significant.

| Peridialytic SBP change [mmHg] | Number of patients | RBV First hour [%] | RBV Second hour [%] | RBV Third hour [%] |
|---|---|---|---|---|
| Decreased between 0-30 | 592 | 96.9 | 94.9 | 93.0 |
| Decreased > 30 | 58 | 96.0 | 93.8 | 91.8 |
| Increased | 192 | 97.3 | 95.5 | 93.7 |

| Group (number of patients) | Intradialytic SBP (mmHg) | Intradialytic nadir SBP (mmHg) |
|---|---|---|
| RBV inside 86-92% 3 hours into dialysis (N=76) | 134.2 ± 16.2 | 114.5 ± 16.1 |
| RBV outside 86-92% 3 hours into dialysis (N=143) | 135.9 ± 20.4 | 117.1 ± 20.3 |
| Difference (95% CI) | -1.7 (-6.7 to +3.3) | -2.5 (-7.5 to +2.4) |
| P-value | 0.5 | 0.3 |

| Group (number of patients) | IDH | Fluid administration | IDH and fluid administration |
|---|---|---|---|
| RBV inside 86-92% at 3 hours into dialysis (N=76) | 13.1 | 16.9 | 4.0 |
| RBV outside 86-92% at 3 hours into dialysis (N=143) | 13.0 | 21.1 | 4.3 |
| P-value | 0.97 | 0.12 | 0.74 |

| HD sessions (number of sessions) | RBV First hour | RBV Second hour | RBV Third hour |
|---|---|---|---|
| With IDH (N=418) | 96.4 (94.5; 98.2) | 94.3 (91.8; 96.8) | 93.2 (90.0; 95.9) |
| Without IDH (N=2406) | 96.6 (94.6; 98.5) | 94.4 (91.8; 97.0) | 92.5 (89.2; 95.5) |

| HD session (number of sessions) | RBV First hour | RBV Second hour | RBV Third hour |
|---|---|---|---|
| With fluid administration (N≈576) | 96.3 (94.2; 98.4) | 94.2 (91.7; 97.3) | 93.3 (90.1; 96.2) |
| Without fluid administration (N=2248) | 96.6 (94.7; 98.5) | 94.4 (91.8; 96.9) | 92.4 (89.2; 95.3) |

| | All patients<br><br>N = 842 | | | Population after exclusion of patients with<br><br>RBVs levels below the favorable ranges | | |
|---|---|---|---|---|---|---|
| Time | HR (95% CI) | P-value | N | HR (95% CI) | P-value |
| First hour | 0.58 (0.42 to 0.79) | <0.001 | 820 | 0.56 (0.41 to 0.77) | <0.001 |
| Second hour | 0.54 (0.39 to 0.75) | <0.001 | 824 | 0.53 (0.38 to 0.73) | <0.001 |
| Third hour | 0.46 (0.33 to 0.65) | <0.001 | 827 | 0.46 (0.32 to 0.65) | <0.001 |

*FIG. 28*

TECHNIQUES FOR DIALYSIS BASED ON RELATIVE BLOOD VOLUME

CROSS-REFERENCE TO RELATED APPLICATION

This application claims priority to U.S. Provisional Patent Application Ser. No. 62/733,485, filed on Sep. 19, 2018, entitled "Ultrafiltration Control via Blood Volume Targets," the contents of which are incorporated herein by reference in their entirety.

FIELD

The disclosure generally relates to a dialysis system, and, more particularly, to techniques for controlling aspects of a dialysis process, for instance, an ultrafiltration rate, based on relative blood volume.

BACKGROUND

Dialysis may be used in the treatment of renal disease. Three principal dialysis methods are hemodialysis (HD), hemodiafiltration (HDF) and peritoneal dialysis (PD). Various unwanted substances may be removed from a patient's blood during a dialysis treatment, including waste products (for instance, urea), toxins, and foreign substances (for instance, prescription drug molecules).

Adequate fluid volume control is one of the major challenges of dialysis. For example, a majority of HD patients are fluid-overloaded. Removal of fluid via ultrafiltration is essential to avoid long-term consequences of fluid overload, such as congestive heart failure, ventricular hypertrophy, or inflammation. However, proper management of dialytic fluid removal is required to avoid intradialytic complications, such as harmful effects on vital organs or intradialytic hypotension (IDH). Accordingly, a goal in dialysis is to achieve a fluid-removal plan in which dialysis treatment sufficiently removes unwanted interstitial fluid, while avoiding removal of too much fluid, and thus improve patient treatment outcomes.

SUMMARY

This Summary is provided to introduce a selection of concepts in a simplified form that are further described in the Detailed Description below. This Summary is not intended to necessarily identify key features or essential features of the claimed subject matter, nor is it intended as an aid in determining the scope of the claimed subject matter.

In accordance with various aspects of the described embodiments is an apparatus, comprising at least one processor and a memory coupled to the at least one processor. The memory comprising instructions that, when executed by the at least one processor, cause the at least one processor to determine a relative blood volume (RBV) value of a patient during a dialysis process, determine ultrafiltration (UF) information based on the RBV value and RBV target information, and provide the UF information to control a UF pump during the dialysis process.

In some embodiments of the apparatus, the RBV target information comprising population-based dialysis data of real patient outcomes of a patient population associated with the patient. In various embodiments of the apparatus, the instructions, when executed by the at least one processor, to cause the at least one processor to present a graphical user interface (GUI) operative to perform at least one of: displaying RBV and UF information of the dialysis treatment or receive a UF deviation range for the dialysis treatment from a user.

In some embodiments of the apparatus, the instructions, when executed by the at least one processor, to cause the at least one processor to determine the UF information to maintain the RBV value within a target RBV range defined by the RBV target information. In exemplary embodiments of the apparatus, the UF information comprising one of: a UF rate (UFR) or a UF goal (UFG).

In various embodiments of the apparatus, the instructions, when executed by the at least one processor, to cause the at least one processor to determine the UF information based on a proportional-integral (PI) process, a process variable of the PI process comprising the RBV value. In some embodiments of the apparatus, a control variable of the PI process comprising the UF information.

In exemplary embodiments of the apparatus, the UF information comprising a UF rate (UFR). In various embodiments of the apparatus, the RBV target information comprising a plurality of RBV time values, each of the plurality of RBV time values comprising a target RBV range at a defined time interval during the dialysis process.

In some embodiments of the apparatus, the instructions, when executed by the at least one processor, to cause the at least one processor to determine the UF information based on at least one constraint, the at least one constraint comprising at least one of: a maximum UF rate (UFR) change, oxygen saturation, blood pressure, or IDH prediction. In various embodiments of the apparatus, the instructions, when executed by the at least one processor, to cause the at least one processor to provide the UF information to a UF pump controller to adjust operation of the UF pump to achieve a UF rate (UFR).

In accordance with various aspects of the described embodiments is a computer-implemented method, comprising, via a processor of a computing device determining a relative blood volume (RBV) value of a patient during a dialysis process performed via a dialysis machine operably coupled to the computing device, determining ultrafiltration (UF) information based on the RBV value and RBV target information, and providing the UF information to control a UF pump during the dialysis process.

In exemplary embodiments of the method, the RBV target information comprising population-based dialysis data of real patient outcomes of a patient population associated with the patient. In some embodiments of the method, comprising determining the UF information to maintain the RBV value within a target RBV range defined by the RBV target information. In various embodiments of the method, the UF information comprising one of: a UF rate (UFR) or a UF goal (UFG).

In some embodiments of the method, the RBV target information comprising a plurality of RBV time values, each of the plurality of RBV time values comprising a target RBV range at a defined time interval during the dialysis process. In various embodiments of the method, comprising determining the UF information based on at least one constraint, the at least one constraint comprising at least one of: a maximum UF rate (UFR) change, oxygen saturation, blood pressure, or IDH prediction.

In accordance with various aspects of the described embodiments is a computer-implemented method for performing a dialysis process using relative blood volume (RBV)-based ultrafiltration (UF) control, the method comprising, via a processor of a computing device operably coupled to a dialysis machine performing the dialysis process, receiving RBV target information comprising population-based dialysis data of real patient outcomes of a patient population associated with the patient, determining an RBV value of a patient during the dialysis process, comparing the RBV value to the RBV target information, and determining UF information to control a UF pump of the dialysis device to maintain the RBV value within a target RBV range defined by the RBV target information.

In some embodiments of the method, controlling the pump comprising adjusting operation of the UF pump to achieve a UF rate (UFR). In some embodiments of the method, comprising determining the UF information to maintain the RBV value within a target RBV range defined by the RBV target information. In various embodiments of the method, the UF information comprising a UF goal (UFG). In some embodiments of the method, the RBV target information comprising a plurality of RBV time values, each of the plurality of RBV time values comprising a target RBV range at a defined time interval during the dialysis process.

In accordance with various aspects of the described embodiments is a computer-implemented method of performing a dialysis treatment, the method comprising, via a processor of a computing device, determining relative blood volume (RBV) values of a patient during the dialysis treatment, comparing the RBV values to RBV target information, and adjusting an ultrafiltration rate (UFR) of the dialysis treatment to maintain future RBV values of the patient during the dialysis treatment within RBV target ranges.

In some embodiments of the method, wherein the RBV target information comprises population-based dialysis data of real patient outcomes of a patient population associated with the patient. In various embodiments of the method, wherein adjusting the UFR comprises adjusting the rate of a UF pump used to perform the dialysis treatment In some embodiments of the method, wherein adjusting UFR comprises increasing UFR. In exemplary embodiments of the method, wherein adjusting UFR comprises decreasing UFR.

BRIEF DESCRIPTION OF THE DRAWINGS

By way of example, specific embodiments of the disclosed machine will now be described, with reference to the accompanying drawings, in which:

FIGS. 6A and 6B depict an RBV-based ultrafiltration (UF) controller graphical user interface (GUI) according to some embodiments.

FIG. 9 illustrates a second logic flow in accordance with some embodiments.

FIGS. 10-29 depict Intradialytic RBV All-Cause Mortality Study graphical information.

4

FIGS. 31A-31D depict Clinical Pilot Study graphical information.

Figure 32:
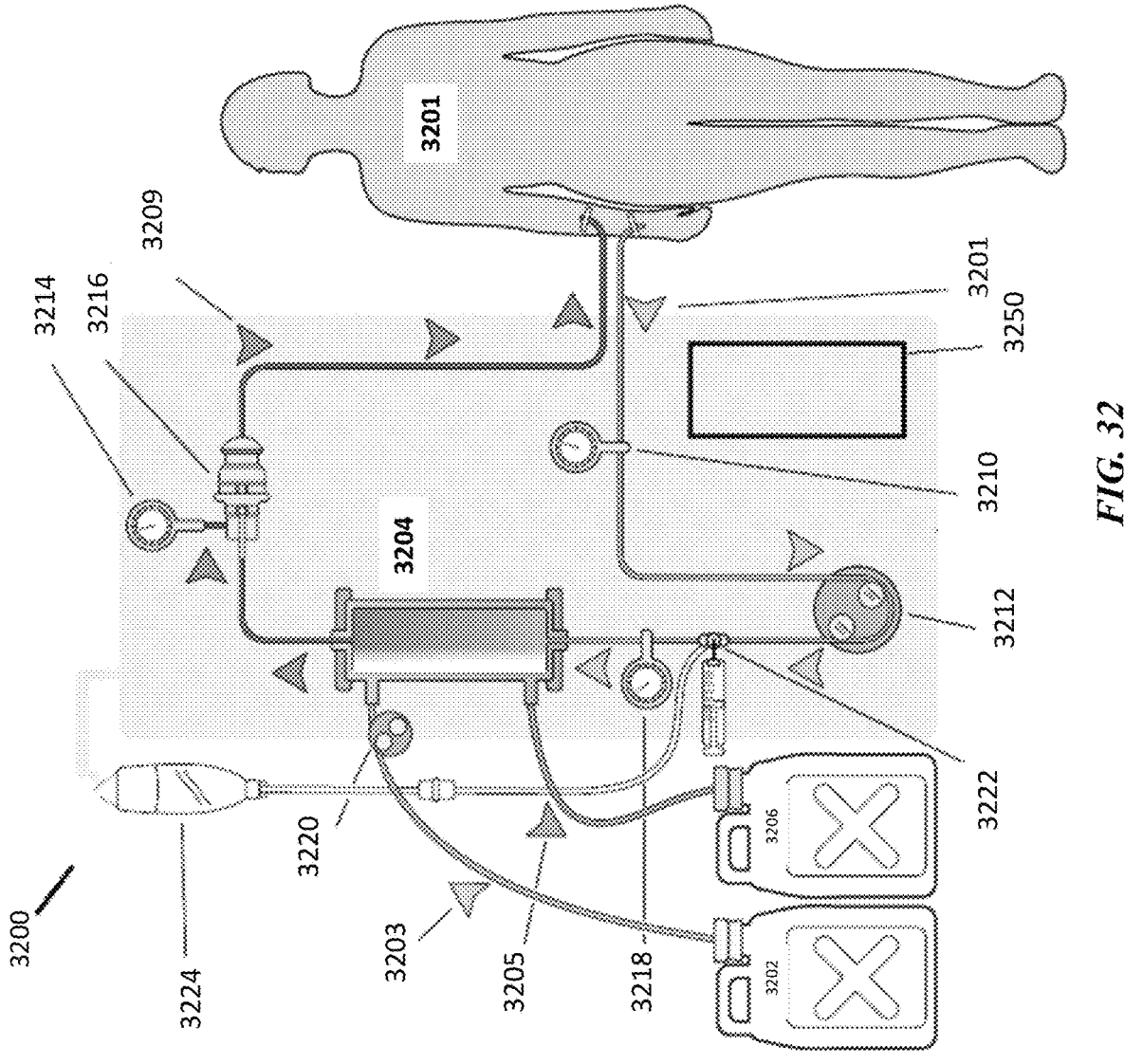

FIG. 32 illustrates an example hemodialysis system.

Figure 33:
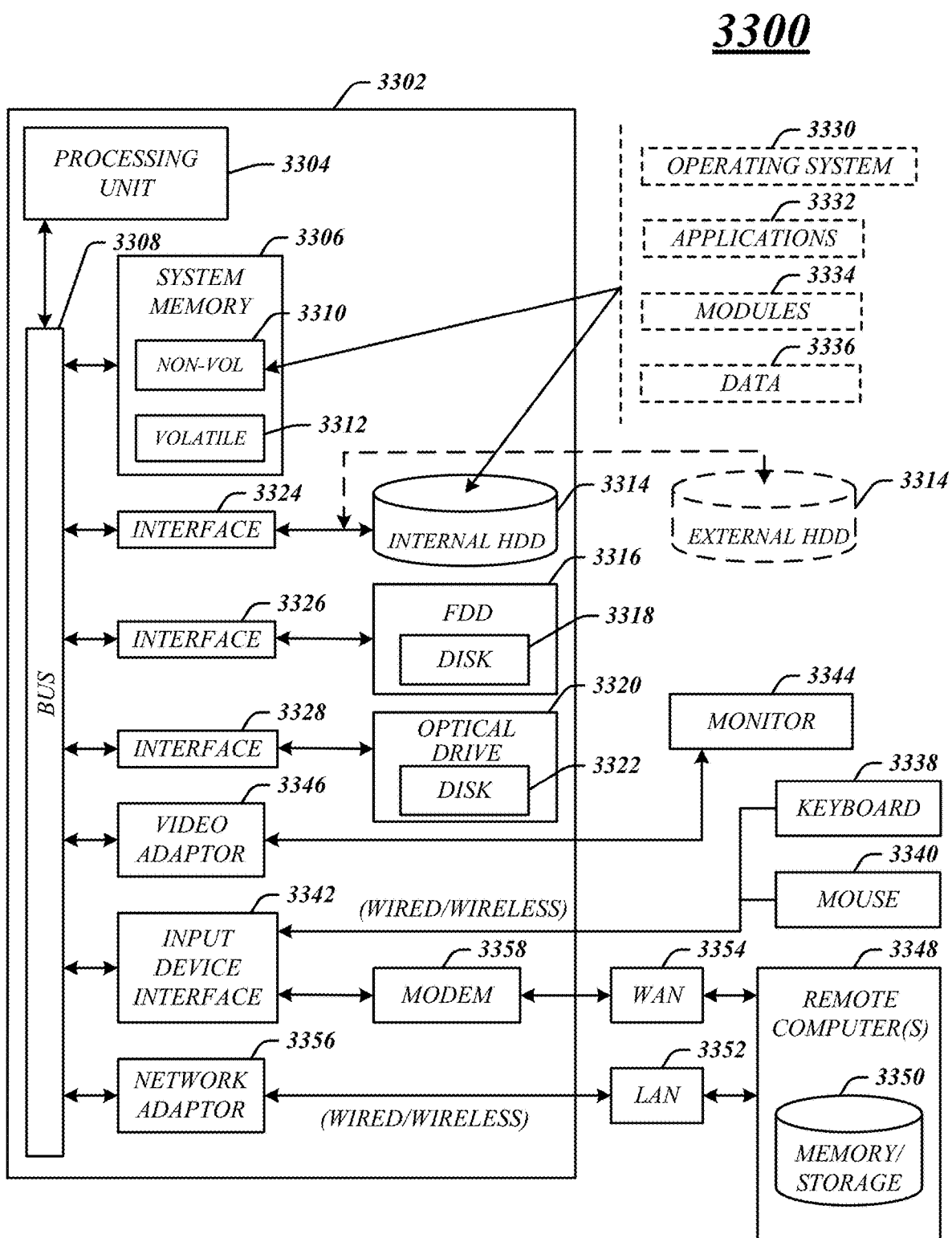

FIG. 33 illustrates an embodiment of a computing architecture according to the present disclosure.

DETAILED DESCRIPTION

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Fluid management is one of the principal functions of hemodialysis, but the progressive increase in mean age and comorbidities among patients on this therapy is associated with diminished clinical status and tolerance to treatment. The short duration of each HD session contributes to the risk of intradialytic morbid events and eventually leads to an inadequate attainment of fluid removal. For example, in most HD sessions, the ultrafiltration rate (UFR) exceeds the refill rate of fluid from the interstitium into the vascular space, resulting in a decline in blood volume, potentially precipitating intradialytic hypotension (IDH) and decreased perfusion of vital organs. Symptomatic IDH affects 20-50% of end stage renal disease (ESRD) patients during their regular HD therapy. This directly reflects on morbidity, as many patients leave treatment with persistent fluid overload, translating ultimately into hypertension, left ventricular hypertrophy, pulmonary congestion, inflammation, and premature death.

Clinical assessment has been the basis of deciding how much fluid to remove during each treatment, but it is generally accepted that this approach is less than ideal. Several technologies have been proposed for objective assessment of fluid status, including measurement of Relative Blood Volume (RBV). RBV devices measure changes in intravascular fluid status of the blood passing through the dialysis lines by monitoring the concentration of whole-blood constituents, such as hemoglobin or hematocrit. These hemoconcentration markers can effectively monitor real time relative changes in blood water concentration, offering the potential for prevention of IDH and improved fluid management. RBV decreases with ultrafiltration (UF), and higher UF rates result in steeper declines in the RBV curve.

Accordingly, various embodiments may generally be directed toward systems, methods, and/or apparatuses for performing a dialysis process in which removal of patient fluid may be based, at least in part, on RBV. In some embodiments, UF properties, such as a UF rate (UFR), a UF goal (UFG), and/or the like may be determined at various time periods during the dialysis process to maintain a patient's RBV within a target RBV value or range over the course of a treatment. As described in more detail in this Detailed Description, patient intradialytic RBV may be associated with dialysis patient morbidity (see, for example, Case Study 1: Intradialytic RBV All-Cause Mortality Study). For instance, specific intradialytic RBV ranges may be associated with all-cause mortality in HD patients (see, for example, Case Study 1: Intradialytic RBV All-Cause Mortality Study). Therefore, maintaining intradialytic RBV within a target RBV value or range at various time periods during a dialysis treatment according to various embodiments may reduce or even eliminate certain dialysis complications, thereby improving patient outcomes.

For example, in some embodiments, a UF Rate Feedback Controller Device software has been developed that, using information provided in real time by the Fresenius 2008T hemodialysis machine and the CLiC® device, identifies an appropriate Relative Blood Volume (RBV) trajectory for each patient (input), thus guiding the UF rate (output) to a beneficial goal within certain ranges of RBV. These ranges are based on previous observational data.

For example, as described in more detail in Case Study 1: Intradialytic RBV All-Cause Mortality Study below, RBV ranges associated with significantly improved survival may be determined. In Case Study 1, a retrospective (January 2012 to December 2016) multi-center (17 U.S. Renal Research Institute clinics) cohort study was done in prevalent, chronic HD patients (see, for example, Case Study 1: Intradialytic RBV All-Cause Mortality Study). After a 6-month baseline period, patients were followed up until the end of the study period. The Crit-Line Monitor (CRM), which provides minute-by-minute hematocrit (Hct) readings and is the standard of care in RRI clinics, was used to obtain RBV readings. RBV was calculated from the change in Hct as $RBV(t) [\%]=100 \cdot Hct(0)/Hct(t)$ (with $Hct(0)$ being the initial Hct and $Hct(t)$ being the current Hct). RBV levels at 1, 2 and 3 hours into the treatment were defined as the mean RBV between minutes 50 and 70, 110 and 130, and 170 and 190, respectively. The relationship between all-cause mortality and RBV was analyzed using Cox proportional hazards models with spline terms for RBV at these three hourly time points, which allowed for identification of hourly RBV ranges associated with significantly improved survival.

Conventional dialysis systems typically use a static UFR and/or UFG. For example, a standard dialysis system may use a UFR profile set at the beginning of treatment that delivers the UFR without factoring in any physiological feedback. Accordingly, conventional systems lack the ability to automatically react to physiological changes in a patient during a dialysis process, such as plasma refill and hemodynamic changes. In addition, alternative conventional dialysis methods are not configured to control UFRs and/or UFGs based on RBV, particularly target RBV ranges demonstrated to provide improved patient outcomes.

Accordingly, described embodiments may provide multiple technological features and advantages over conventional systems, including improvements in computing technology. One non-limiting example of a technological advantage may include providing dialysis processes with automated, feedback-based control of dialytic UF, such as UFR and/or UFG, based on physiological characteristics of a patient, including intradialytic RBV. For example, a logic device configured to manage a dialysis process may be or may include a controller operative to receive patient RBV information and to determine a UFR and/or a UFG to achieve a particular patient RBV during a time period of a dialysis treatment. Another non-limiting example of a technological advantage may include improving patient dialysis treatment outcomes based on controlling UF during a dialysis treatment using RBV information derived from population-based dialysis data of real patient outcomes (see, for example, FIGS. 2 and 3). In this manner, embodiments may provide additional non-limiting technological advantages of performing dialysis via delivering UF that allows for removal of a prescribed UF volume while minimizing intradialytic complications and maximizing long-term patient outcomes in a more effective and accurate process than available through conventional methods.

In this description, numerous specific details, such as component and system configurations, may be set forth in order to provide a more thorough understanding of the described embodiments. It will be appreciated, however, by one skilled in the art, that the described embodiments may be practiced without such specific details. Additionally, some well-known structures, elements, and other features have not been shown in detail, to avoid unnecessarily obscuring the described embodiments.

In the following description, references to "one embodiment," "an embodiment," "example embodiment," "various embodiments," etc., indicate that the embodiment(s) of the technology so described may include particular features, structures, or characteristics, but more than one embodiment may and not every embodiment necessarily does include the particular features, structures, or characteristics. Further, some embodiments may have some, all, or none of the features described for other embodiments.

As used in this description and the claims and unless otherwise specified, the use of the ordinal adjectives "first," "second," "third," etc. to describe an element merely indicate that a particular instance of an element or different instances of like elements are being referred to, and is not intended to imply that the elements so described must be in a particular sequence, either temporally, spatially, in ranking, or in any other manner.

Figure 1:
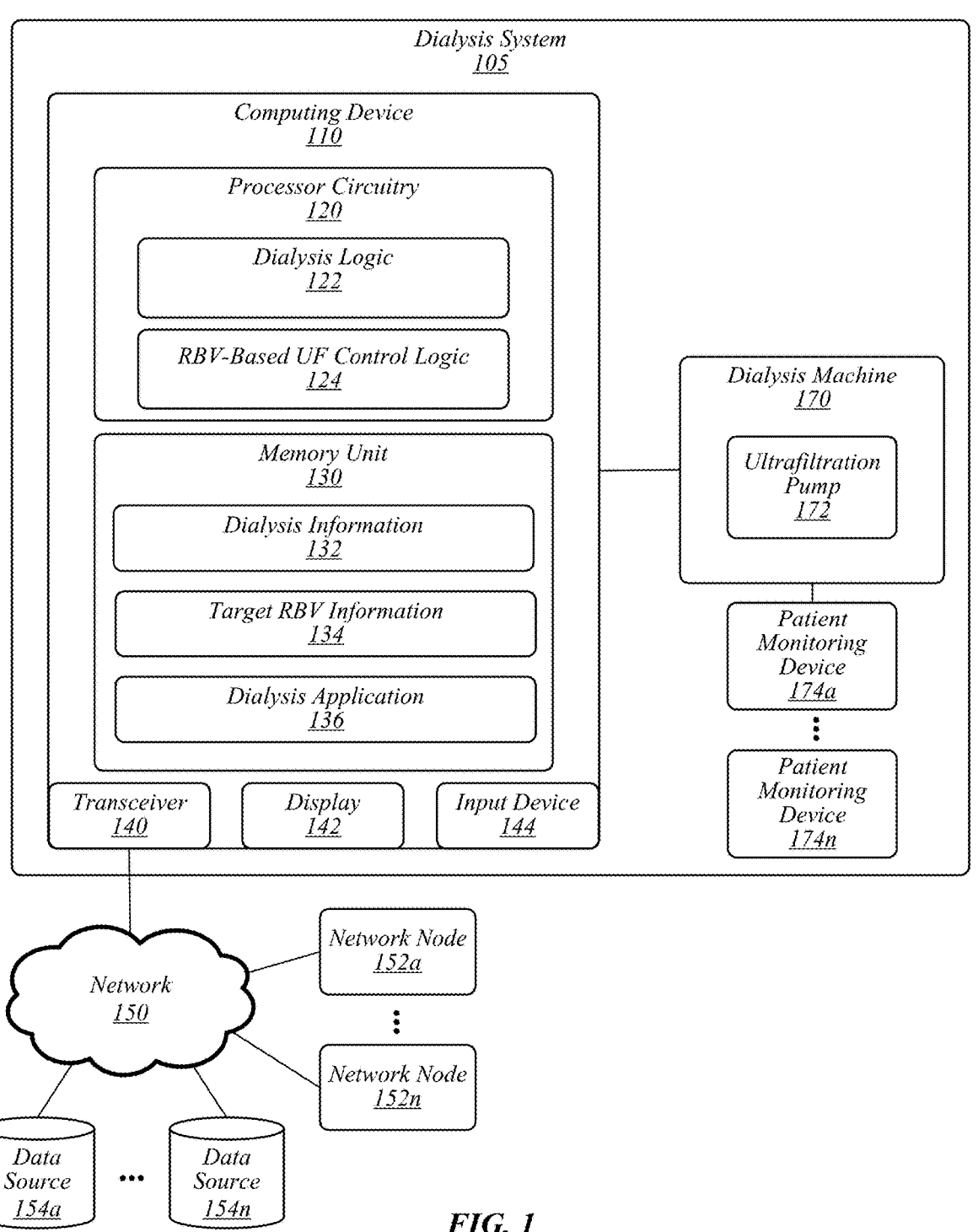
FIG. 1 illustrates an example of a first operating environment that may be representative of some embodiments of the present disclosure.

FIG. 1 illustrates an example of an operating environment 100 that may be representative of some embodiments. As shown in FIG. 1, operating environment 100 may include a dialysis system 105 associated with a dialysis machine 170. In some embodiments, dialysis machine 170 may include various components, such as a UF pump 172. In various embodiments, dialysis machine 170 may be or may include an HD dialysis system. For example, dialysis machine 170 may be or may include a Fresenius 2008T HD machine available from Fresenius Medical Care, Waltham, Massachusetts, United States of America. Although HD is used in examples in this Detailed Description, embodiments are not so limited, as other types of dialysis systems and treatments capable of being performed according to some embodiments are contemplated herein.

In various embodiments, dialysis system 105 may include a computing device 110 communicatively coupled to dialysis machine 170. Computing device 110 may be configured to manage, among other things, operational aspects of dialysis machine 170 to perform a dialysis treatment on a patient. Although only one computing device 110 and dialysis machine 170 are depicted in FIG. 1, embodiments are not so limited. In various embodiments, the functions, operations, configurations, data storage functions, applications, logic, and/or the like described with respect to computing device 110 may be performed by and/or stored in one or more other computing devices (not shown), for example, coupled to computing device 110 via a network 150 (i.e., network nodes 152a-n). A single computing device 110 and dialysis machine 170 are depicted for illustrative purposes only to simplify the figure. For example, computing device 110 may operate to partially or wholly operate a dialysis process for a plurality of dialysis machines 170 coupled to computing device 110, for instance, via network 150. Embodiments are not limited in this context.

Computing device 110 may include a transceiver 140, a display 142, an input device, 144, and/or processor circuitry 120 communicatively coupled to a memory unit 130. Processor circuitry 120 may be, may include, and/or may access various logics for performing processes according to some embodiments. For instance, processor circuitry 120 may include and/or may access a dialysis logic 122 and/or a RBV-Based UF control logic 124. Processing circuitry 120, dialysis logic 122, and/or RBV-Based UF control logic 124, and/or portions thereof, may be implemented in hardware, software, or a combination thereof. As used in this application, the terms "logic," "component," "layer," "system," "circuitry," "decoder," "encoder," "control loop," and/or "module" are intended to refer to a computer-related entity, either hardware, a combination of hardware and software, software, or software in execution, examples of which are provided by the exemplary computing architecture 3300. For example, a logic, circuitry, or a module may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, a control loop, a proportional-integral-derivative (PID) controller, combinations of any of the foregoing, and/or the like.

Although dialysis logic 122 and RBV-Based UF control logic 124 are depicted in FIG. 1 as being within processor circuitry 120, embodiments are not so limited. For example, dialysis logic 122, the RBV-Based UF control logic 124, and/or any component thereof, may be located within an accelerator, a processor core, an interface, an individual processor die, implemented entirely as a software application (for instance, a dialysis application 136) and/or the like. In some embodiments, computing device 110 and/or components thereof may be an embedded or integral component of dialysis machine. For instance, processor circuitry 120, dialysis logic 122, RBV-Based UF control logic 124, and/or portions thereof may be arranged in or otherwise integral to dialysis machine 170.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store dialysis information 132 and/or RBV information 134. In some embodiments, dialysis information 132 may include information generated during a dialysis process, including dialysis machine 170 operational information and/or patient physiological information. Operational information may include a UFR, a UFG, treatment time, operating parameters, and/or the like. Patient physiological information may include temperature, heart rate, RBV, oxygen saturation, blood pressure, intradialytic hypotension (IDH) information (for instance, predicted IDH information), and/or the like. Embodiments are not limited in this context.

In various embodiments, dialysis machine 170 may be operably coupled to various patient monitoring devices 174*a-n* operative to monitor various physiological characteristics of a patient undergoing dialysis treatment. For example, monitoring devices 174*a-n* may be or may include a blood volume (BV) monitoring device and/or a hematocrit measuring device such as a Crit-Line® Monitor (CLM), available from Fresenius Medical Care, Waltham, Massachusetts, United States of America. In general, a CLM may be an inline monitor operative to measure hematocrit, oxygen saturation, and/or changes in blood volume during dialysis treatment. Although a CLM may be used in some examples, embodiments are not so limited, as any technique, device, apparatus, system, process, and/or the like for measuring and/or predicting patient physiological characteristics, such as BV and/or RBV, capable of operating according to some embodiments is contemplated herein. In various embodiments, monitoring devices 174*a-n* may include a fluid management monitoring tool such as the CliC® device available from Fresenius Medical Care, Waltham, Massachusetts, United States of America. A CliC® device may non-invasively measure certain patient physiological characteristics, such as absolute hematocrit and continuous oxygen saturation. Accordingly, in some embodiments, information monitored by one or more of monitoring devices 174*a-n* may be or may be used to determine RBV and/or other physiological characteristics for a patient over the course of a dialysis treatment.

In some embodiments, target RBV information 134 may include desired RBV values for a particular patient over the course of the dialysis treatment. In some embodiments, target RBV information 134 may be or may include population-based RBV information. In various embodiments, the population-based RBV information may be or may include RBV ranges for improved patient outcomes based on various factors including, without limitation, hazard ratios (HRs), morbidity values, mortality values, complication rates, and/or the like. In various embodiments, target RBV information may include a target RBV range for time periods of a dialysis process.

Figure 2:
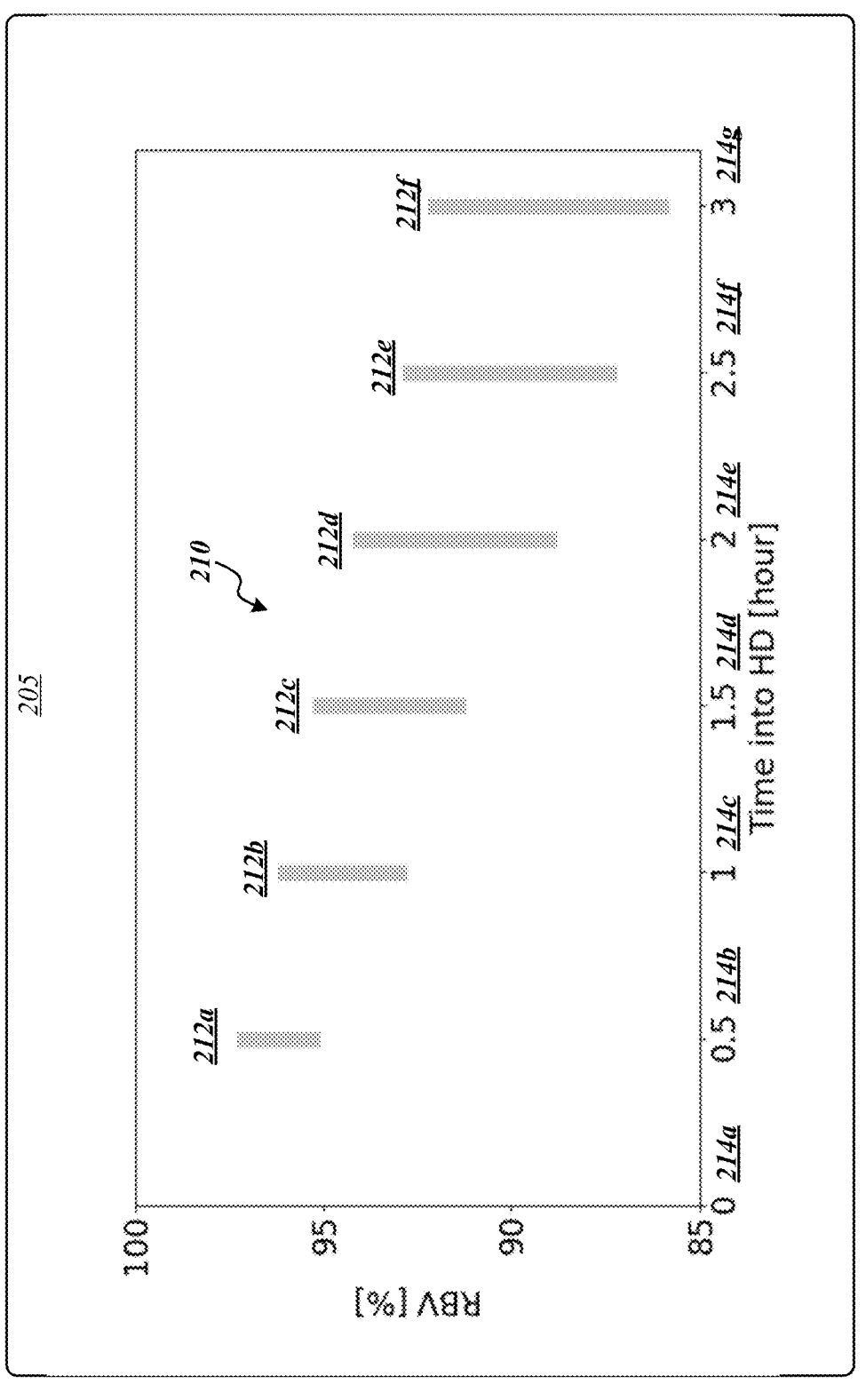
FIG. 2 illustrates target relative blood volume (RBV) information according to some embodiments.

Referring to FIG. 2, therein is depicted a graph 205 of illustrative target RBV information in the form of an RBV curve 210. As shown in FIG. 2, RBV curve 210 may include target RBV ranges 212*a-f*, one for each of time period 214*a-f*. Although time periods 214*a-f* are in half-hour increments, time periods 214*a-f* may have any duration according to some embodiments, including, without limitation, 10 seconds, 30 seconds, 1 minute, 5 minutes, 10 minutes, 15 minutes, 20 minutes, 30 minutes, 45 minutes, 1 hour, 1 hour and 30 minutes, 2 hours, and any value or range between any two of these values (including endpoints).

In various embodiments, target RBV ranges 212*a-f* may include favorable RBV ranges determined from a population of patients, for example, in one or more clinical trials. In some embodiments, target RBV ranges 212*a-f* may include RBV values for the population of patients with improved HRs, for instance, HRs below a threshold value, such as HRs of all-cause mortality of <1.0.

Figure 3:
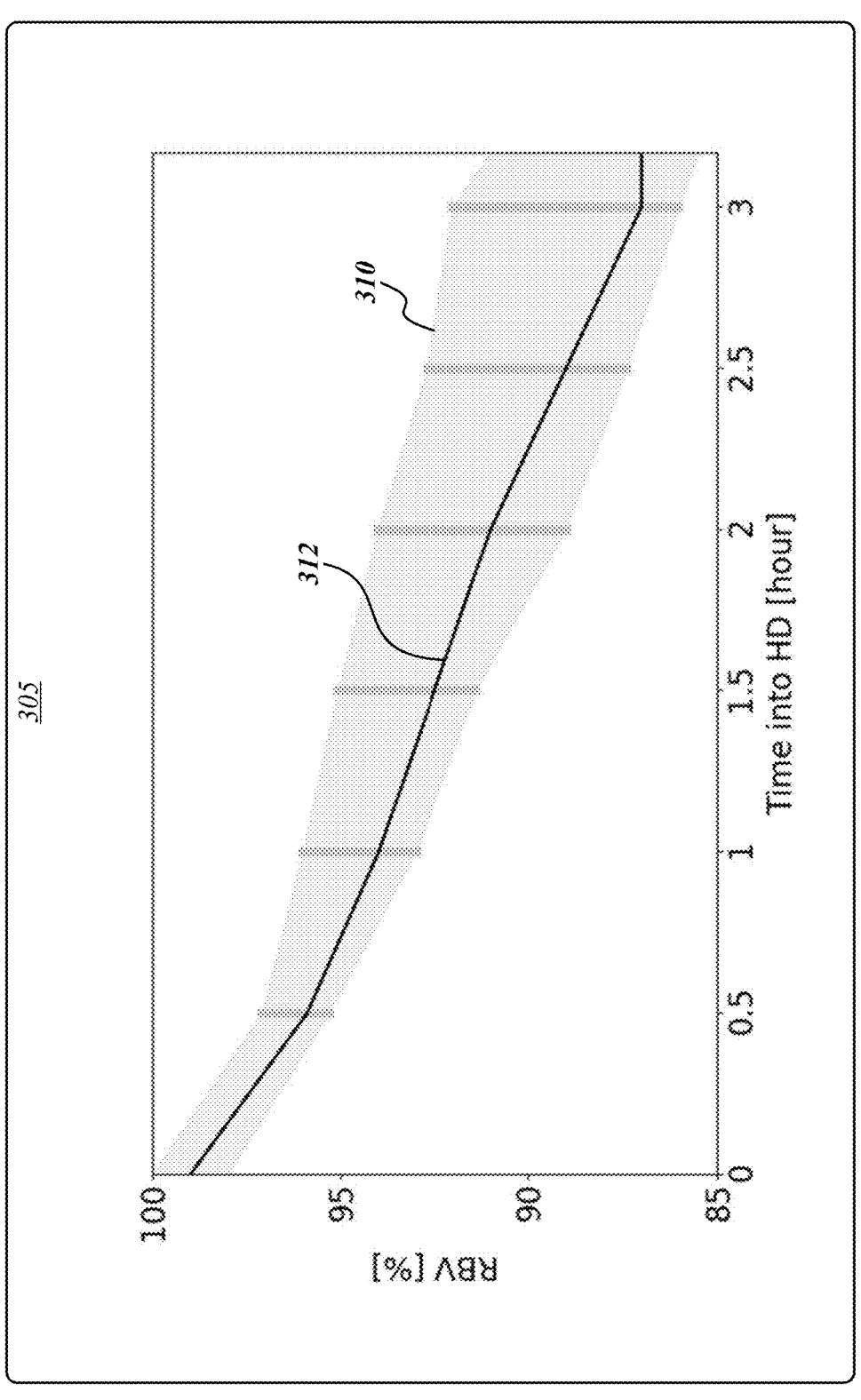
FIG. 3 illustrates target relative blood volume (RBV) information according to some embodiments.

Referring to FIG. 3, therein is depicted a graph 305 of illustrative target RBV information. As shown in FIG. 3, target RBV ranges, such as target RBV ranges 212a-f, may be used to generate a target area or "favorability tube" 310 by connecting the top of the ranges 212a-f and the bottom of the ranges. In some embodiments, a target RBV curve 312 may be determined, for example, as a straight or substantially straight line running through the ranges of target area 310 or otherwise fitted through the median or the average of the ranges of target area 310.

The population used to generate target RBV information 134 may have various characteristics, such as age, gender, disease state, fluid removal volume, complications, and/or the like. In various embodiments, target RBV information 134 may include a plurality of RBV curves and/or ranges, for example, each associated with a certain set of population characteristics. Accordingly, in some embodiments, a patient undergoing a dialysis treatment according to some embodiments may use target RBV information associated with their individual characteristics, subgroup, and/or the like. For example, a 60-year-old female patient may use an RBV curve 312 determined for female patients between the ages of 50 and 60 years. Embodiments are not limited in this context. In various embodiments, RBV-based UF control logic 124 may receive patient information (for instance, physical information, disease information, historical treatment information, and/or the like) and determine one or more optimal target RBV curves, ranges, or other structures to be used for RBV-based UF control during treatment of the patient. In general, RBV-based UF control logic 124 may operate according to some embodiments as feedback controller designed to guide a patient's RBV curve into predefined target ranges during a dialysis treatment.

In various embodiments, dialysis logic 122, for example, via dialysis application 136, may operate to perform a dialysis process on a patient via dialysis machine 170, such as an HD treatment. For example, dialysis logic 122 may receive dialysis treatment information, such as patient characteristics, dialysis prescription information, and/or the like to perform a dialysis process on a patient. RBV-Based UF control logic 124 may operate to perform computer-assisted UF control by managing UF properties during the dialysis treatment based on RBV value of the patient and target RBV information. UF properties may include a UFR and/or a UFG. In some embodiments, RBV-Based UF control logic 124 may operate, for example, via dialysis application 136, to control UF pump 172 to achieve target UF properties.

Figure 4:
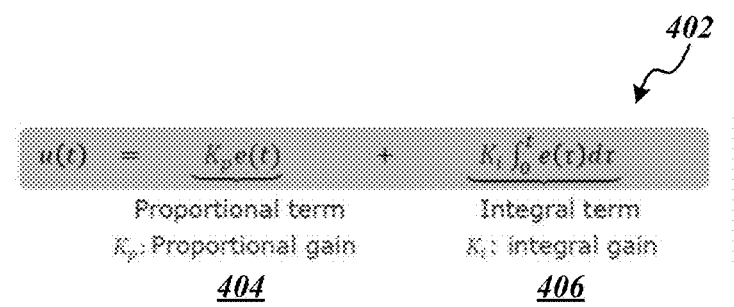
FIG. 4 illustrates proportional-integral (PI) control elements according to some embodiments.
Figure 4:
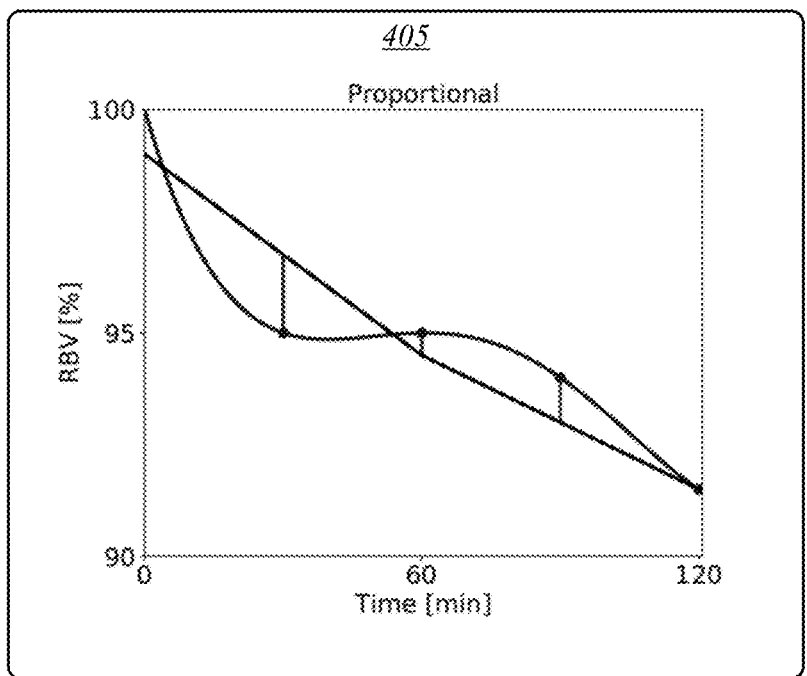
Figure 4:
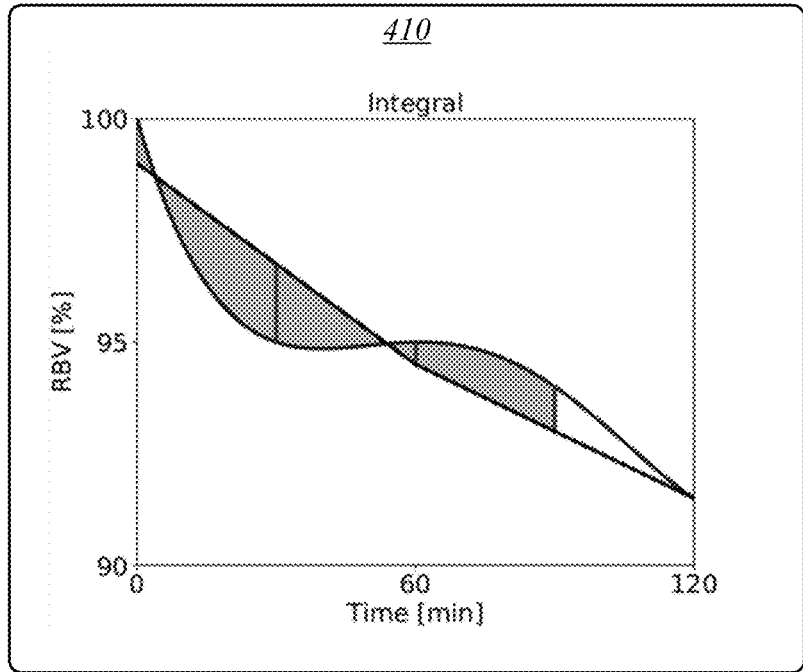

In some embodiments, UF control logic 124 may be or may include a control element, such as PID control loop. FIG. 4 depicts PI control loop information according to some embodiments. In various embodiments, the PI control loop may determine UFR at time t (u(t)) according to equation 402, having a proportional gain term 404, depicted graphically in graph 405, and an integral gain term 406, depicted graphically in graph 410. Embodiments are not limited in this context.

The PID controller may continuously take the error value (the deviation of a (measured) process variable from a desired value) to adjust the control variable such that the process variable follows the desired values. In some embodiments, the PID controller may operate as a PI controller (for instance, a PID controller with the derivative (D) term set to zero). In some embodiments, the process variable is the patient's RBV level (for example, calculated from the patient's hematocrit value (the physiologic variable)), and the adjusted control variable is the UF rate. In general, the PI controller operates such that, if the process variable decreases when the control variable increases, then the control variable will be increased if the process variable is larger than the desired value and vice versa. The PI controller has two terms to calculate the size of the adjustment: The proportional term 404 considers the value of the error only at the current time point whereas the integral term 406 considers the history of the error by summing up all previously measured errors. Both terms have a gain (proportional gain and integral gain) to adjust performance.

Accordingly, in some embodiments, RBV-based UF control logic 124 may operate a closed loop controller having patient RBV values as a feedback variable. For example, RBV-based UF control logic 124 may set a UFR for UF pump 172 (for instance, starting at an initial value). Patient RBV values may be continuously monitored and provided to the RBV-based UF control logic (for instance, PID or PI control loop) and compared to the target RBV information. RBV-based UF control logic 124 may adjust the UFR to set or maintain the patient RBV within the target RBV range for the particular time period.

In some embodiments, UF control may be completely automated by RBV-based UF control logic 124. In various embodiments, operator assistance may be used to confirm or change UFR and/or UFG values determined by RBV-based UF control logic 124. For example, RBV-based UF control logic 124 may determine at the 1-hour mark that the UFR should be increased from x to y. A graphical user interface (GUI) prompt, alert, message, or other signal may be used to prompt a nurse or other operator to verify the increase (see, for example, FIGS. 6A, 6B, and 7). Alternatively, the operator may enter a specific UFR range or other operating parameters, such as UFR change thresholds, UFG ranges, and/or the like.

Figure 5:
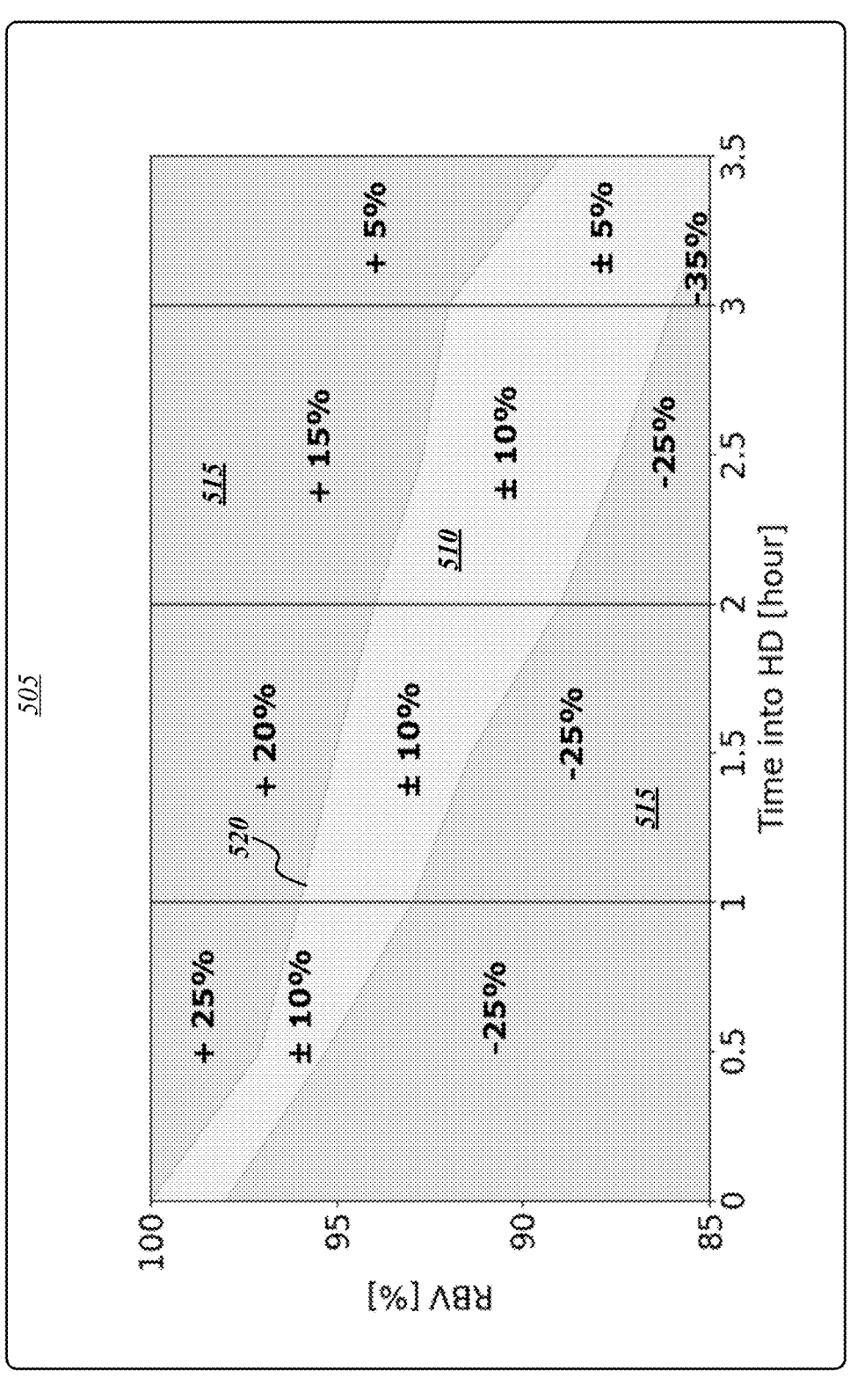
FIG. 5 illustrates target relative blood volume (RBV) information according to some embodiments.

In various embodiments, RBV-based UF control logic 124 may operate with various constraints, such as PID controller constraints, to reduce or even eliminate negative results of changing UFR. Non-limiting examples of constraints may include UF boundaries (see, for example, FIG. 5), UFR change thresholds, oxygen saturation, blood pressure, and/or (predicted) IDH. In some embodiments, UFR change thresholds may include a maximum relative change in UFR (for instance, +/−75% of a prescribed UFR) and/or a maximum allowed change in UFR (for instance, a maximum milliliter/hour change). FIG. 5 depicts a graph 505 of illustrative UFR change limits or boundaries for a favorability tube 520 showing allowed UFR changes relative to a prescribed UFR according to some embodiments within a favorability tube 510 and outside of the favorability tube 515. Table 1 depicts the information of graph 505 in tabular form:

TABLE 1

| Elapsed Treatment Time (min) | Maximum Allowed Change (relative to prescribed UF rate) | |
| | RBV Inside Favorability Tube | RBV Outside Favorability Tube |
| --- | --- | --- |
| 15-60 | +/−10% | +/−25% |
| 60-120 | +/−10% | +20%, −25% |
| 120-180 | +/−10% | +15%, −25% |
| >180 | +5%, −10% | +5%, −35% |

As long as a patient's RBV remains within favorability tube 310, the patient's RBV will pass through the RBV target ranges. Accordingly, if the RBV is inside favorability tube 310, the controller (for instance, RBV-based UF control logic 124) may be configured to make only smaller adjustments to the UF rate. The maximum allowed changes to the UFR may be defined as percentages of the prescribed UFR and/or absolute UFR increases/decreases. Outside of the favorability tube 310, larger adjustments may be allowed, for example, since these might be necessary to get the patient's RBV into the favorability tube. On top of these relative bounds, the controller may be programmed to observe the parameters defined in Table 1.

Accordingly, in some embodiments, the maximum allowed UFR changes may be reduced as treatment progresses. For example, the controller may only increase the UFR by a maximum of 5% during the final phase of the treatment (>180 minutes). However, it is allowed to substantially reduce the UF rate (up to 35%) in patients with an RBV below the target tube, in order to bring RBV into the desired range, because reductions in UFR are associated with improved hemodynamic stability and may pose little or no risk to the patient.

In some embodiments, dialysis information 132 may include constraint information for a course of treatment, such as which constraints are active, threshold values, constraint actions, and/or the like. For example, dialysis information 132 may indicate that the UFR change limits depicted in FIG. 5 are active and one or more constraint action to take if a UFR change outside of the tolerated range is determined by RBV-based UF control logic 124. For example, a constraint action may be to maintain a previous UFR, go to the maximum/minimum UFR within the allowed thresholds (for instance, if the threshold UFR change is +20% and the determined UFR change is +30%, perform the maximum 20% change), trigger an alarm, combinations thereof, and/or the like. Embodiments are not limited in this context.

For example, for an oxygen saturation constraint, RBV-based UF control logic 124 may prevent increasing the UFR in the case of low (for instance, below an absolute threshold) and/or falling oxygen saturation levels (for instance, a percentage change over a specified duration). For instance, for catheter-based central-venous oxygen saturation, an absolute threshold of about 44% and a relative threshold of 7% over 5 minutes may be used. In another instance, for AVF arterial oxygen saturation, an absolute threshold of about 86% and a relative threshold of 5% over 5 minutes may be used. Embodiments are not limited in this context. In general, an arterial oxygen saturation below 86% and central-venous oxygen saturation below 44% for at least 5 minutes may be considered "low," and a decrease in oxygen saturation by more than 5 percentage points (for central-venous oxygen saturation) or more than 7 percentage points (for arterial oxygen saturation) over the preceding 5 minutes may be considered "falling."

In another example, for a blood pressure constraint, RBV-based UF control logic 124 may constrain changes in UFR based on absolute blood pressure values and/or a blood pressure trend (for instance, a change over a time period). For example, RBV-based UF control logic 124 may permit an otherwise allowable UFR adjustment within a specified threshold blood pressure range. Outside of the specified threshold blood pressure range, RBV-based UF control logic 124 may permit increases in UFR, but not decreases in UFR.

In a further example, an IDH constraint may be used based on predicted IDH (for instance, predicted at certain time intervals, such as every 1 minute-30 minutes). In various embodiments, RBV-based UF control logic 124 may decrease a UF rate responsive to a (predicted) IDH value being outside of a threshold.

In some embodiments, RBV-based UF control logic 124 may perform various validations on all user-provided inputs to ensure they are reasonable. Any UF rate suggested by the controller may be within the initially defined hard limits (UFR and UFG deviation). In some embodiments, RBV-based UF control logic 124 may be disabled or paused if the prescribed UFG violates the internal upper UFR limit, for example, of 13 mL/kg/hour.

In various embodiments, RBV-based UF control logic 124 may perform internal checks on its operation. If no initial UFR suggestion can be calculated (for instance, due to insufficient data availability) or if any of the calculations do not pass these internal checks, no UFR suggestion may be produced, and RBV-based UF control logic 124 may automatically enter Fallback Mode. In Fallback Mode, RBV-based UF control logic 124 may suggest that the treatment be continued with the current UFG setting.

Data received from patient monitoring devices 174*a-n*, such as CLiC® data, may be pre-processed by RBV-based UF control logic 124, for example, so that no UFG or UFR suggestions are based on erroneous or questionable data. In some embodiments, RBV-based UF control logic 124 may not suggest any change in UF rate if the required input data are not sufficient. Further, there is an option to prevent the controller from suggesting an increase in the UF rate in the presence of low or falling oxygen saturation levels. The nurse can turn this option on or off in the GUI. Other constraints described herein may also limit or disable changes to UFG and/or UFR.

Figure 6A:
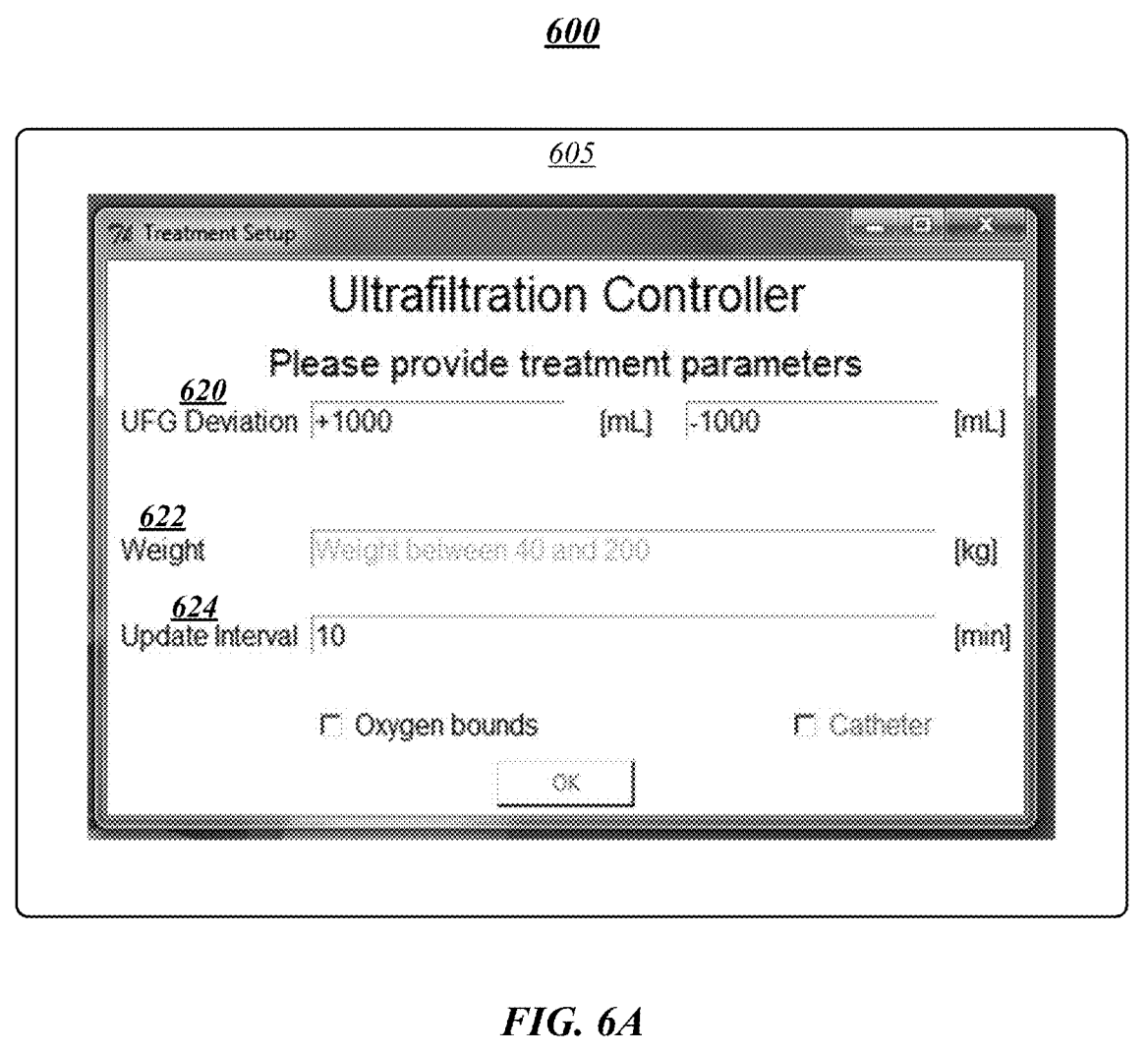
Figure 6B:
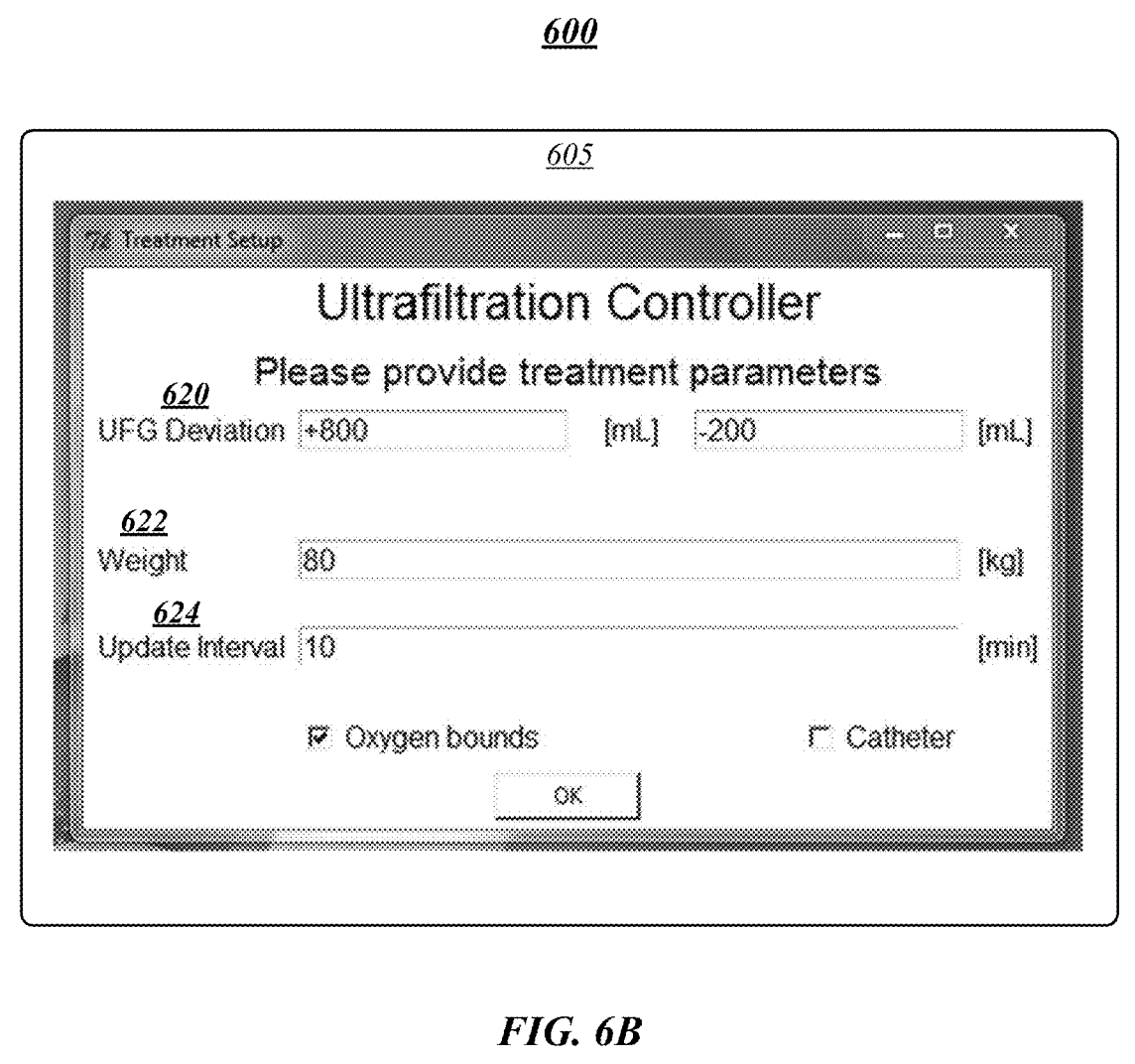
Figure 7:
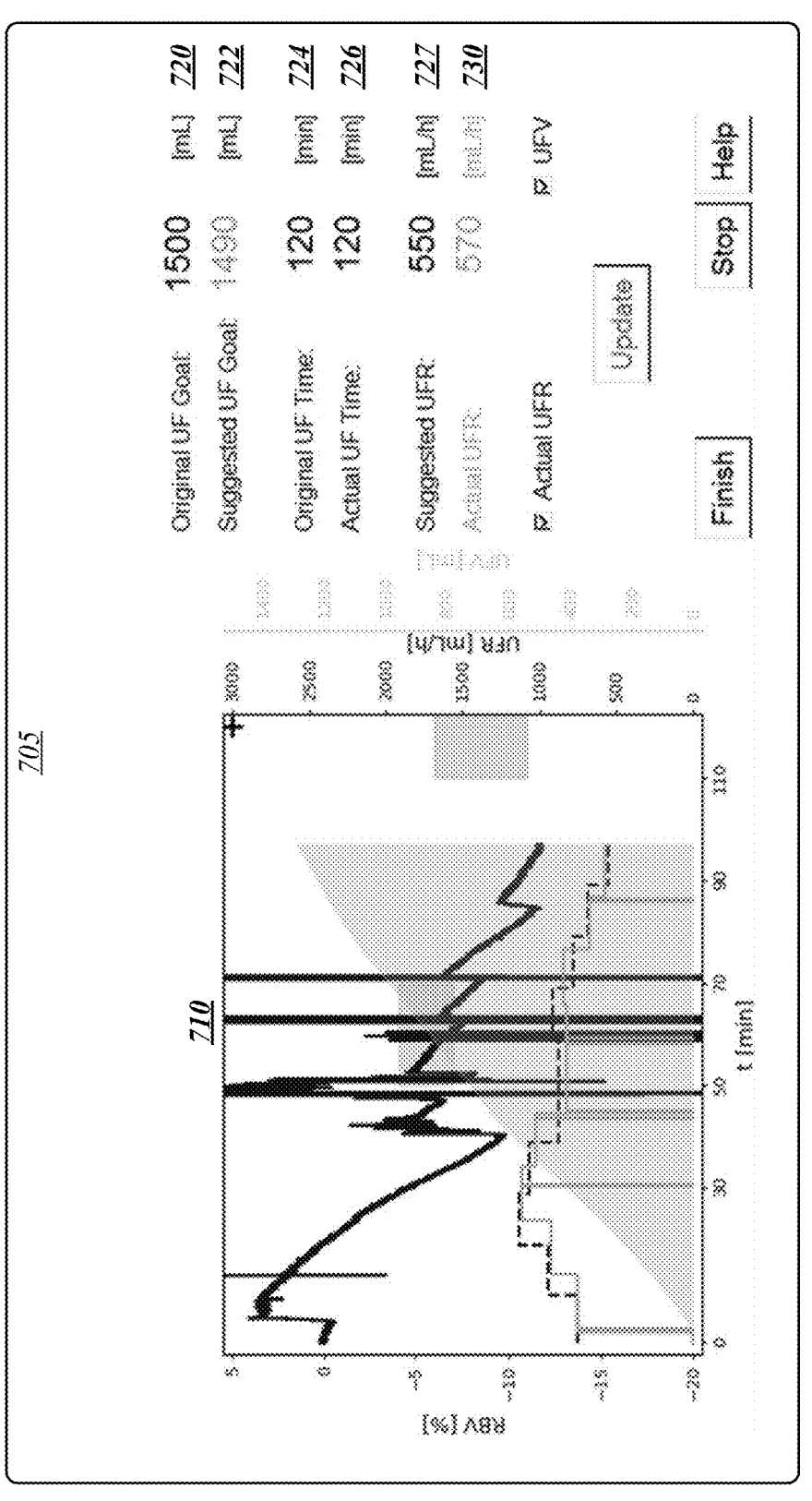
FIG. 7 depicts a RBV-based UF control display GUI according to some embodiments.

In various embodiments, dialysis application 136, alone or in combination with dialysis logic 122 and/or RBV-based UF control logic 124, may provide various GUI interfaces for presenting and/or receiving information relating to RBV-based UF control of a dialysis treatment. FIGS. 6A and 6B depict a UF controller input GUI interface 605 according to some embodiments. As shown in FIGS. 6A and 6B, a UF controller input GUI interface 605 may include objects for receiving treatment parameters, such as ultrafiltration (for instance, UFG) deviation values 620, weight 622, update interval 624, and/or the like. Embodiments are not limited to the input/data objects depicted in FIGS. 6A and 6B, as input/data objects to receive and/or display any type of information for RBV-based UF control of a dialysis treatment may be presented via UF controller input GUI interface 605. FIG. 7 depicts an RBV-based UF control GUI interface 705 according to some embodiments. RBV-based UF control GUI interface 705 may be configured to present information associated with RBV-based UF control during a dialysis treatment, such as a graph 710 of RBV vs. time, an original UF goal 720, a suggested UF goal (for instance, determined by RBV-based UF control logic 1240), original UF time 724, actual UF time 726, suggested UFR 727, and actual UFR 730. In this manner, an operator, such as a nurse, may view and manage RBV-based UF control in real-time or substantially real-time.

Included herein are one or more logic flows representative of exemplary methodologies for performing novel aspects of the disclosed architecture. While, for purposes of simplicity of explanation, the one or more methodologies herein are shown and described as a series of acts, those skilled in the art will understand and appreciate that the methodologies are not limited by the order of acts. Some acts may, in accordance therewith, occur in a different order and/or concurrently with other acts from that shown and described herein.

For example, those skilled in the art will understand and appreciate that a methodology could alternatively be represented as a series of interrelated states or events, such as in a state diagram. Moreover, not all acts illustrated in a methodology may be required for a novel implementation. Blocks designated with dotted lines may be optional blocks of a logic flow.

A logic flow may be implemented in software, firmware, hardware, or any combination thereof. In software and firmware embodiments, a logic flow may be implemented by computer executable instructions stored on a non-transitory computer readable medium or machine readable medium. The embodiments are not limited in this context.

Figure 8:
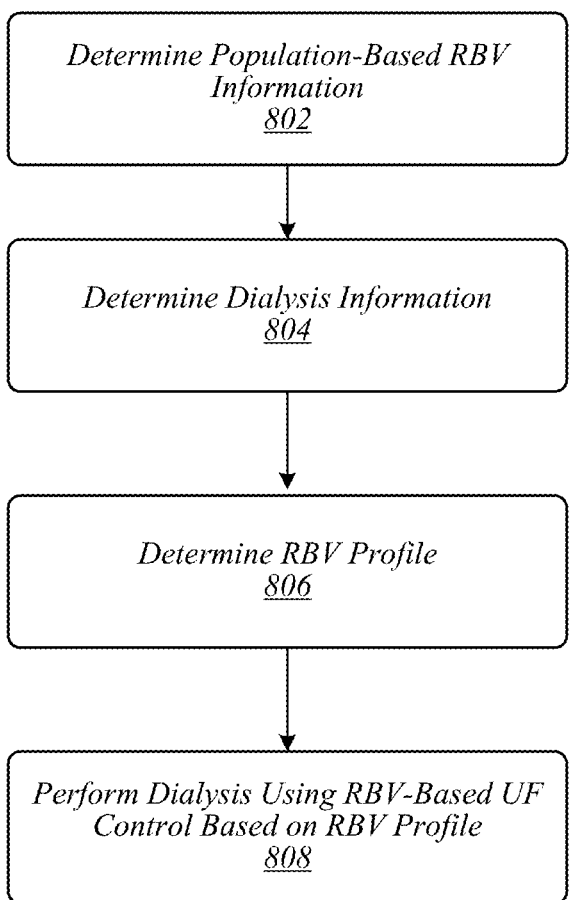
FIG. 8 illustrates a first logic flow in accordance with some embodiments.

FIG. 8 illustrates an embodiment of a logic flow 800. The logic flow 800 may be representative of some or all of the operations executed by one or more embodiments described herein, such as computing device 110 and/or components thereof. In some embodiments, logic flow 800 may be representative of some or all of the operations of determining an RBV profile for a patient according to some embodiments.

At block 802, logic flow 800 may determine population-based RBV information 802. In some embodiments, population-based RBV information 802 may be or may include population-specific target RBV information, such as target RBV curve 312, determined based on one or more analyses. In some embodiments, the analyses may include real-world clinical trials (see, for example, Case Study 1: Intradialytic RBV All-Cause Mortality Study), in-silico clinical trials (see, for example, Case Study 2: In-Silico Case Study), combinations thereof, and/or the like. For example, a clinical trial of RBV ranges and patient outcomes may be performed to determine one or more target RBV curves for a population, subgroup, and/or the like. A subgroup may include any type of divisible group of the clinical trial population, such as age, gender, complications (for instance, congestive heart failure, diabetes, UFG, and/or the like). Accordingly, in some embodiments, target RBV information 132 may include a library of target RBV ranges or curves that may be associated with individual patients based on patient physical characteristics, treatment regimens, and/or the like. In some embodiments, RBV information 132 may be stored locally, for example, in memory 130 of computing device 110. In other embodiments, RBV information 132 may be accessible via a network, cloud, or other storage environment. In this manner, a patient receiving treatment at a particular location may be able to be treated using a wide range of RBV target structure to determine an optimal match for the patient.

Logic flow 800 may determine dialysis information at block 804. For example, dialysis information 132 such as patient characteristics, dialysis prescription information, treatment parameters, RBV-based UF control parameters, constraint information, and/or the like may be accessed by RBV-based UF control logic 124.

At block 806, logic flow 800 may determine an RBV profile. For example, RBV-based UF control logic 124 may determine a RBV target curve 312 that corresponds with the patient from a library of target RBV information. For example, a RBV target curve 312 may be determined that matches or substantially matches patient characteristics or patient subgroup characteristics.

Logic flow 800 may perform dialysis using RBV-based UF control based on the RBV profile at block 808. For example, dialysis application 136 may perform a dialysis operation via dialysis machine 170 with RBV-based UF control operating to maintain patient RBV values within the range specified by the target RBV curve determined in block 808. In this manner, a patient may receive dialysis treatment with RBV-based UF control optimized for their individual or subgroup characteristics.

FIG. 9 illustrates an embodiment of a logic flow 900. The logic flow 900 may be representative of some or all of the operations executed by one or more embodiments described herein, such as computing device 110, dialysis machine 170, and/or components thereof. In some embodiments, logic flow 900 may be representative of some or all of the operations of performing a dialysis treatment according to some embodiments At block 902, dialysis treatment may be started by logic flow 900. For example, dialysis logic 122 may start, via dialysis application 136, a dialysis treatment process of a patient using dialysis machine 170. The dialysis process may start with an initial UFG and UFR. In some embodiments, RBV-based UF control may be initialized on computing device 110. Various dialysis information 132 may be provided to computing device, for example, at certain time intervals (for instance, every 0.5 seconds to 10 minutes) or frequency (for instance, 0.5 Hz-5.0 Hz). Non-limiting examples of dialysis information 132 from dialysis machine 170 may include HD machine timestamp, HD machine ID, Patient ID, UF rate, cumulative UF volume, UF goal, blood volume processed, blood pressure (BP), remaining time of dialysis, remaining UF time, and/or the like. Dialysis information 132 may also be received from patient monitoring devices 174a-n, such as a CLM and/or CliC® device. Illustrative and non-restricting examples of dialysis information from patient monitoring devices 174a-n may include timestamp, counter, hematocrit, hemoglobin concentration, oxygen saturation, blood volume information, vitals information, and/or the like. In some embodiments, dialysis information 132 from dialysis machine 170 and patient monitoring devices may be processed by RBV-based UF control logic 124 to calculate a proposed UFG and/or UFR to steer the RBV of the patient into the target RBV range.

The prescribed UFR is the prescribed UFG or UF volume divided by the entire treatment time. In some embodiments, the dialysis information 132 may include the prior treatment post-HD weight of the patient and, optionally, the maximum allowed deviation (+/−) in the prescribed UFG (for example, +/− about 1000 mL per clinic policy).

Logic flow 900 may determine whether an evaluation period has expired at block 904. For example, the patient RBV may be checked at discrete time intervals, such as at every minute to every 20 minutes. In some embodiments, the evaluation time period may be about 10 minutes. In some embodiments, the evaluation period may be different based on a phase or duration of the dialysis treatment. For instance, a first evaluation period may be about 15 minutes followed by 10-minute intervals for the remainder of the dialysis treatment. Embodiments are not limited in this context.

At block 906, logic flow 900 may determine a patient RBV value. For example, RBV-based UF control logic 124 may determine a patient RBV value based on dialysis information, for example, obtained from a patient monitoring device 174a-n. In some embodiments, the RBV value may be determined based on patient hematocrit values, for instance, determined by a CliC® or similar device. The patient RBV value may include the RBV of the patient at a particular time interval.

Logic flow 900 may determine UF information at block 908. For example, RBV-based UF control logic 124, for instance, via a PI control loop, may determine a recommended UFG. RBV-based UF control logic 124 may determine a recommended UFG based on target RBV information 134 (such as target RBV curve 312) so that the patient RBV is within a target RBV range at a particular time interval.

In some embodiments, logic flow 900 may take one or more constraints into account when determining UF information. For example, based on the patient RBV value, RBV-based UF control logic 124 may determine to increase the UFG by 10%. However, a blood pressure constraint may prevent that increase if, for example, the patient blood pressure is outside of a threshold value. If a constraint is triggered, the recommended UFG may be generated based on a constraint action, which may include maintaining the current UFG.

At block 910, logic flow 900 may change the UFR to achieve the UFG determined in block 908. In some embodiments, a recommended UFR may be determined based on the recommended UFG and the remaining time in the dialysis treatment (for instance, the UFR required to meet the recommended UFG in the remaining time). For example, RBV-based UF control logic 124, alone or in combination with dialysis application 136, may change the operation of UF pump 172 to change the UFR. In some embodiments, the change in UFR may be denied due to constraints and/or the recommended change in UFR being outside of maximum change thresholds (see, for example, Table 1 and FIG. 5).

In some embodiments, operator intervention may be required to change the UFR or other UF operating parameters. In such embodiments, an operator may be alerted that a change in UF operating parameters, such as UFR, is being recommended. For example, from 60 seconds before to 60 seconds after each of the scheduled update timepoints (or evaluation periods), an "Update Controller" button on a GUI may flash, along with an acoustic signal, to alert the operator (for instance, a dialysis nurse) that the controller is ready to attempt to generate a UF rate recommendation for evaluation and, if applicable, implementation. When the operator selects the "Update Controller" button, the GUI displays an updated UFR and the corresponding UFG (based on the remaining UF time). The operator then decides whether or not to implement this suggestion. To implement the controller's suggestion, in some embodiments, the operator may enter the suggested UFG (rather than the UFR) into the HD machine (for example, via GUI 605) (changing the UFR on the machine may cause the treatment time to be adjusted while keeping the UFG, which is not desired). Changing the UFG always keeps the remaining treatment time the same and adjusts the UF rate, which is the desired change.

Rather than entering the controller's suggestion, the operator may also decide to enter a different UFG or UFR or make no change at all. If the operator were to miss hitting the "Update Controller" button during the allowed time period, the UF rate would remain unchanged (again, unless the nurse decided to implement a change), and the controller would produce a new UF rate recommendation at the next regularly scheduled update timepoint.

Accordingly, if the operator accepts the recommended UF goal at block 912, logic flow may change the UFR to achieve the UFG at block 910. Otherwise, logic flow may maintain the previous UFR (and UFG) at block 914.

Case Study 1: Intradialytic RBV all-Cause Mortality Study

The Intradialytic RBV All-Cause Mortality Study was performed to determine, inter alia, an association between intradialytic RBV and mortality.

In the Intradialytic RBV All-Cause Mortality Study, RBV was recorded once/min during a 6-month baseline period; all-cause mortality was noted during follow-up. RBV at 1, 2 and 3 hours (h) into HD served as a predictor of all-cause mortality during follow-up. In particular, 842 patients were studied. During follow-up (median 30.8 months), 249 patients (29.6%) died. The following hourly RBV ranges were associated with improved survival: first hour, 93-96% (hazard ratio (HR) 0.58 (95% confidence interval (CI) 0.42-0.79)); second hour, 89-94% (HR 0.54 (95% CI 0.39-0.75)); third hour, 86-92% (HR 0.46 (95% CI 0.33-0.65)). In about one-third of patients, the RBV was within these ranges and in two-thirds it was above. Subgroup analysis by median age (≤/>61 years), sex, race (white/nonwhite), pre-dialysis systolic blood pressure (SBP) (≤/>130 mmHg) and median interdialytic weight gain (≤/>2.3 kg) showed comparable favorable RBV ranges. Patients with a 3-h RBV between 86 and 92% were younger, had higher ultrafiltration volumes and rates, similar intradialytic average and nadir SBPs and hypotension rates, lower post-dialysis SBP and a lower prevalence of congestive heart failure when compared with patients with an RBV>92%. In the multivariate Cox analysis, RBV ranges remained independent and significant outcome predictors.

In general, the Intradialytic RBV All-Cause Mortality Study concluded that specific hourly intradialytic RBV ranges were associated with lower all-cause mortality in chronic HD patients.

Figure 10:
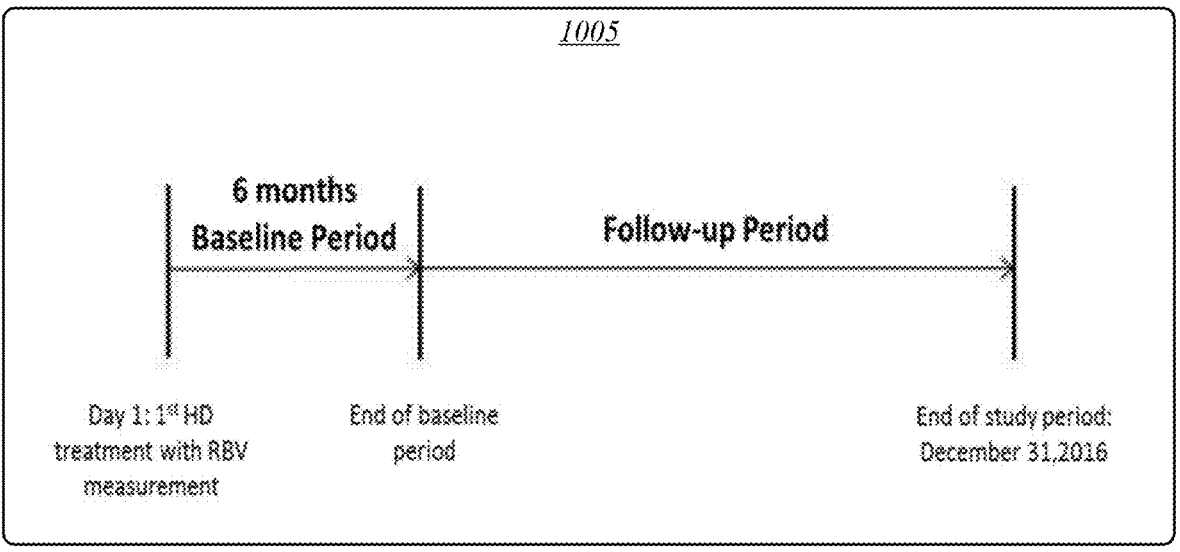

The Intradialytic RBV All-Cause Mortality Study was a multicenter observational retrospective study conducted in maintenance HD patients from 17 facilities of the Renal Research Institute (RRI) of New York, New York, United States. The CLM was deployed to the RRI dialysis clinics on a rolling basis and is the standard of care. A 6-month baseline period and an up to 54-month follow-up period were defined on a patient level (see FIG. 10, which depicts the baseline and follow-up periods). The first treatment with eligible CLM data was as the start date of the baseline period. All patients who had at least 10 eligible CLM recordings during the baseline period were included in the study. A treatment time of <200 min was the only exclusion criterion. Patient characteristics were assessed during baseline. All-cause mortality was recorded during follow-up.

The RBV (expressed in percent of the blood volume at the start of dialysis) at time t was calculated as follows:

$$RBV \text{ (%) at time } t = 100 \times HCT_0/HCT_t.$$

$HCT_0$ and $HCT_t$ are the hematocrits at the start and at a given time t during HD, respectively. Hematocrit was measured quasi-continuously using the CLM, which reported the RBV once/min. Patients' RBVs were calculated per treatment and then averaged across all treatments per patient and subsequently across patients. RBVs at 1, 2 and 3 h into the HD session were used as outcome predictors. To that end, RBV data was averaged between minutes 50 and 70, 110 and 130 and 170 and 190, respectively.

In the Intradialytic RBV All-Cause Mortality Study, blood pressure was automatically measured every 30 min oscillometrically. Average pre-dialysis, post-dialysis and intradialytic systolic blood pressure (SBP) were calculated and nadir SBP and IDH rate reported; IDH was defined as intradialytic SBP <90 mmHg. Intradialytic SBP during baseline was available for 181 treatments in 219 patients.

Congestive heart failure (CHF), diabetes mellitus (DM) and chronic obstructive pulmonary disease (COPD) were documented using International Classification of Diseases, Ninth Revision, codes in the patients' electronic health records.

Descriptive statistics comprised means (+/− standard deviation) for continuous variables and percentages for categorical variables. To explore the association between all-cause mortality and RBV at 1, 2 and 3 h, the Intradialytic RBV All-Cause Mortality Study used Cox proportional hazards models with spline terms, allowing for modeling of nonlinear effects of RBV as a continuous variable and its relationship with all-cause mortality at these three hourly time points. This spline analysis allowed for the identification of hourly RBV ranges associated with hazard ratios (HRs) significantly <1 ('favorable') or >1 ('unfavorable'), respectively.

For additional analysis, patients were stratified into two groups as those being within the 'favorable' 3-h RBV range or not. Survival characteristics were compared using Kaplan-Meier plots, log-rank tests and Cox proportional hazards models. Minimally and fully adjusted Cox models complemented the crude survival analysis. The minimally adjusted model included age, sex, CHF and COPD. In addition, the fully adjusted model included serum albumin and hemoglobin, the neutrophil:lymphocyte ratio (NLR; an inflammatory marker), UFR, pre-dialysis SBP, diabetes and race. Patients were censored in the event of kidney transplantation, transfer to a non-RRI facility, dialysis treatment modality change, or end of follow-up.

Baseline descriptive statistics, group differences and 95% confidence intervals in patients within or outside the 'favorable' 3-h RBV range, respectively, were also reported. To further explore these findings and to account for possible bias considering only 3 h and not the full treatment time, the association between all-cause mortality and RBV by relative elapsed treatment time, with total treatment time defined as 100% was also examined. The Intradialytic RBV All-Cause Mortality Study used 25, 50, 75 and 100% of treatment time elapsed by averaging the RBV between 21-30, 46-55, 71-80 and 91-100% of the total treatment time, respectively. Additionally, the association between RBV slope and all-cause mortality was also examined. The RBV slope was computed using simple linear regression with an intercept at 100% RBV (per definition the initial RBV). A sensitivity analysis excluding patients with RBVs below the favorable hourly RBV ranges was also conducted.

Figure 11:
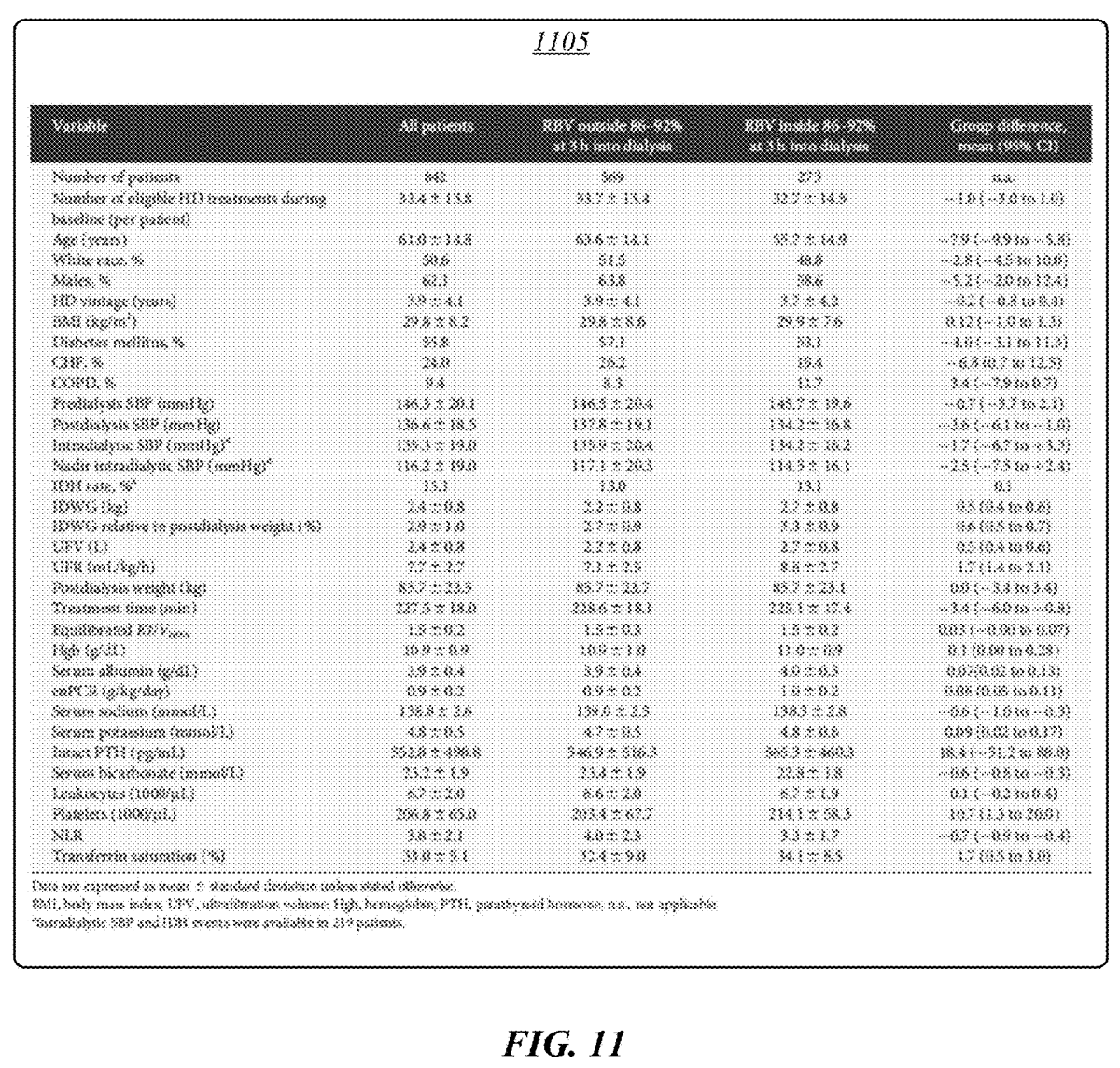

The Intradialytic RBV All-Cause Mortality Study studied 842 patients with a total of 28,119 dialysis sessions with eligible RBV recordings during a 6-month baseline, resulting in 33.4±13.8 eligible sessions per patient (see table 1105 of FIG. 11). Age was 61±14.8 years, dialysis vintage was 3.9±4.1 years, 50.6% were white, 62.1% were male, 55.8% had diabetes, 24% had CHF and 9.4% had COPD. Intradialytic RBVs were 97.9±1.9, 94.8±2.6 and 93.1±3.3% after 1, 2 and 3 h, respectively.

Figure 13:
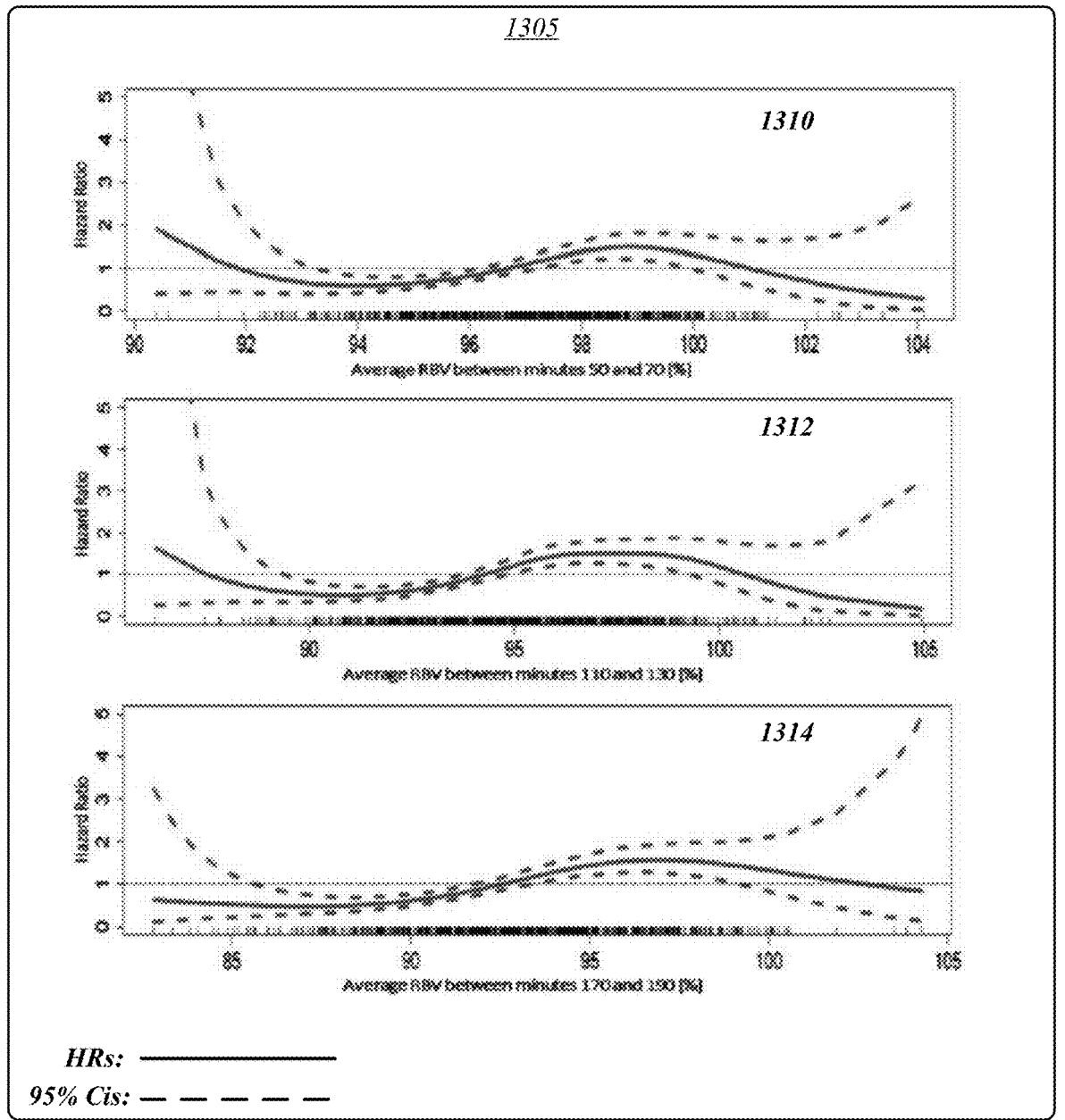
Figure 14:
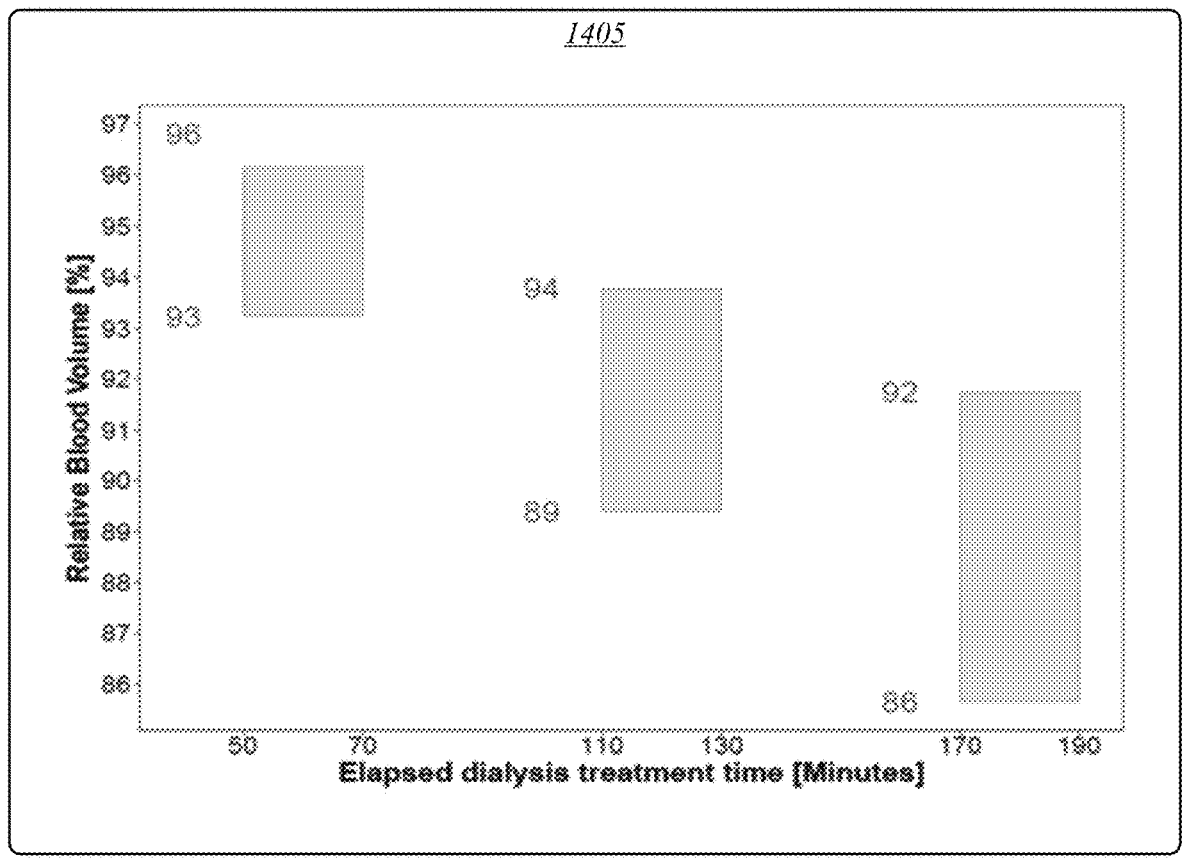

During the median follow-up of 30.8 months, 249 patients (29.6%) died. HRs for all-cause mortality were significantly <1.0 in patients with 1-h RBV 93-96%, 2-h RBV 89-94% and 3-h RBV 86-92%. Approximately 65% of the patients attained RBVs above, 32% within, and ~2.5% below these RBV ranges (see table 1205 of FIG. 12). RBV ranges associated with HRs significantly >1.0 were 97-100% (1 h), 95-99% (2 h) and 93-99% (3 h) (see graphs 1310, 1312, and 1314 of FIG. 13 and graph 1405 of FIG. 14). Referring to FIG. 13, therein is depicted HRs and CIs of achieved RBV levels after 1 hour (graph 1310), 2 hours (graph 1312), and 3 hours (graph 1314), with tick marks on the x-axis representing individual patients. Graph 1405 of FIG. 14 depicts intradialytic hourly RBV ranges that are associated with HRS significantly <1.0 for all-cause mortality.

Figure 15:
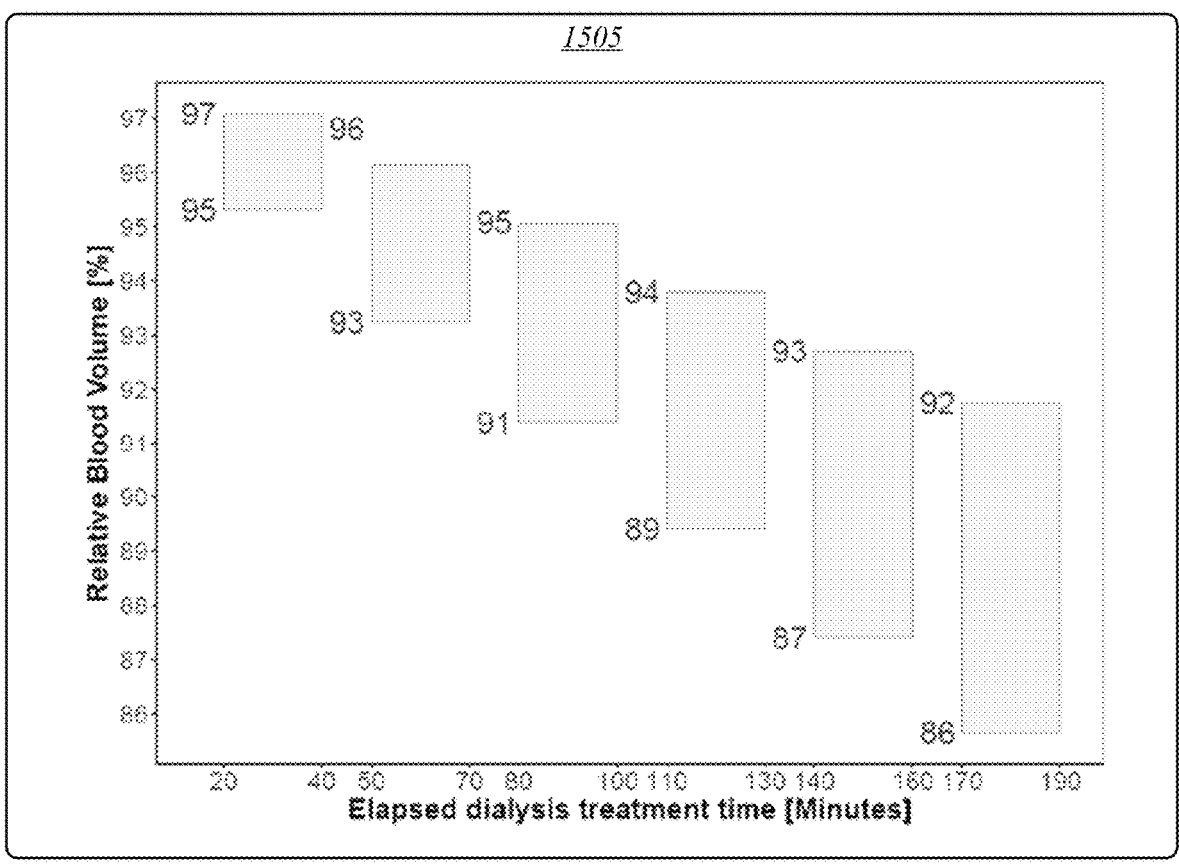
Figure 17:
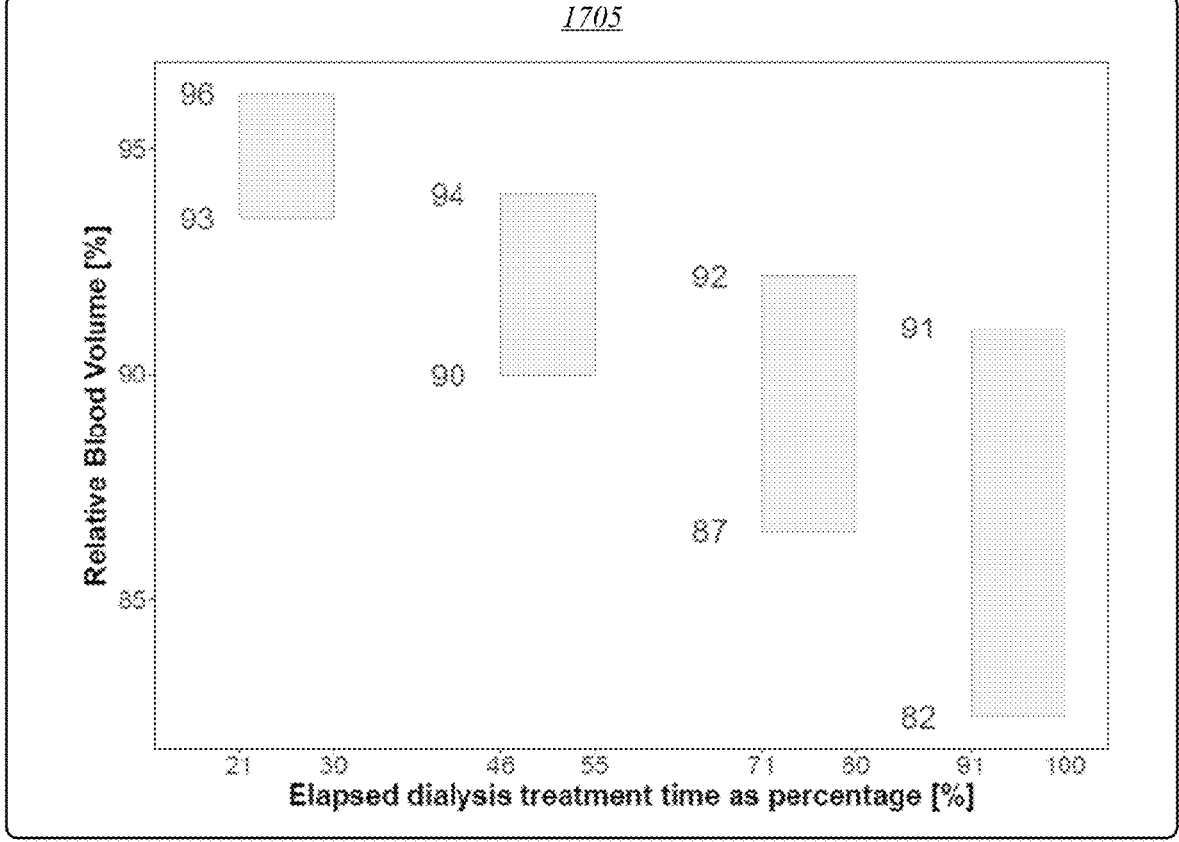

Half-hourly favorable RBV ranges are shown as supplementary data in graph 1505 of FIG. 15. Multivariate Cox analysis corroborated the lower HRs for all-cause mortality in those patients whose RBV fell inside these RBV ranges (see table 1605 of FIG. 16). Analysis by percent of elapsed treatment time instead of by hours showed materially identical results (see graph 1705 of FIG. 17). Subgroup analyses by median age (≤/>61 years), race (white, nonwhite), sex, pre-dialytic SBP (≤/>130 mmHg) and interdialytic weight gain (IDWG) (≤/>2.3 kg) showed comparable favorable RBV ranges (see table 1805 of FIG. 18).

Figure 19:
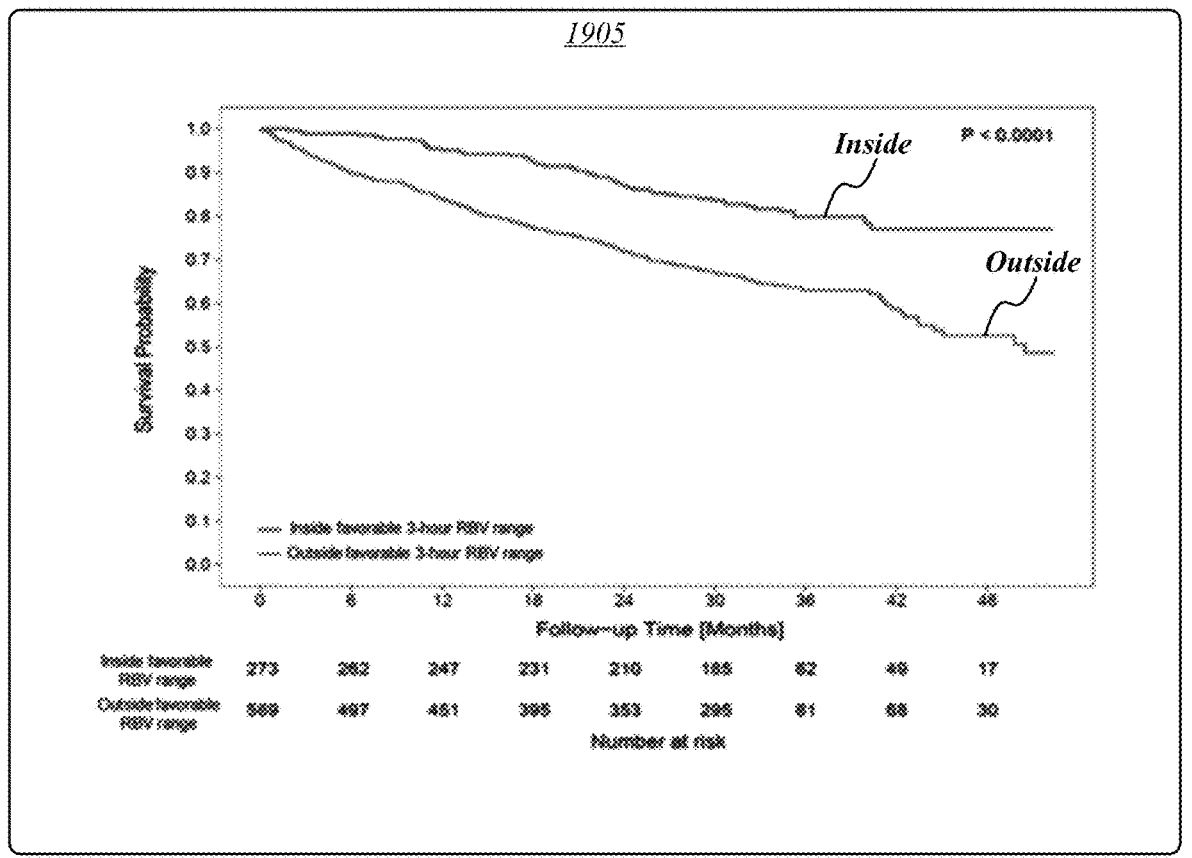
Figure 20:
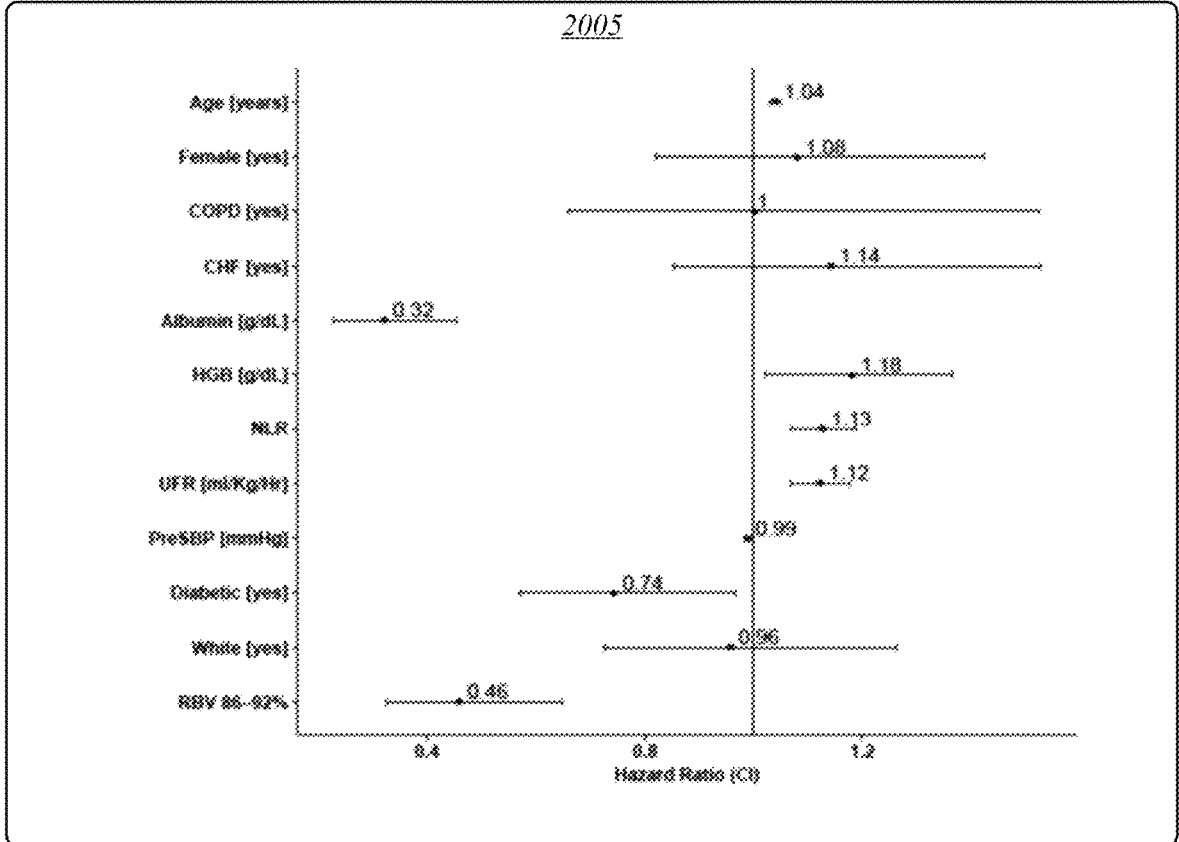

Kaplan-Meier analysis and Cox proportional hazards models indicated a significantly better survival in patients with 3-h RBVs inside 86-92% compared with those patients outside this range (see graph 1905 of FIG. 19 and graph 2005 of FIG. 20).

Figure 21:
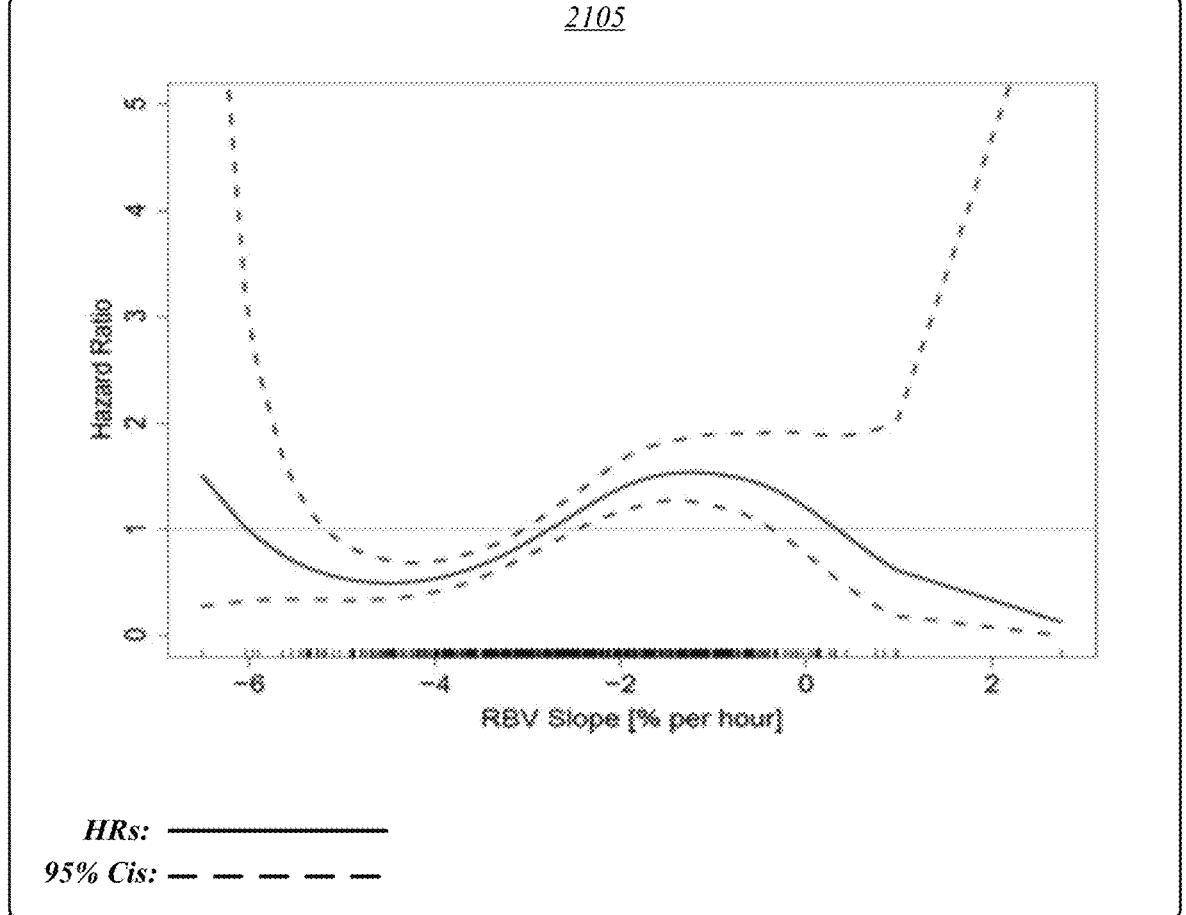

Analysis on the RBV slope and all-cause mortality showed significantly increased HR, with a slope between 2.47 and 0.34%/h, and significantly reduced HR with a slope from 5.18 to 3.04%/h (see graph 2105 of FIG. 21)

The Intradialytic RBV All-Cause Mortality Study compared clinical, laboratory and treatment variables between patients who did and did not attain the 3-h RBV of 86-92% (see table 1105 of FIG. 11). RBVs of 273 patients (32.5%) were within this 3-h RBV range, while 554 patients (65.8%) had RBVs >92% and 15 patients (1.8%)<86%. Patients outside the 86-92% 3-h RBV range were older (63.6+/−15.9 versus 55.7+/−14.1 years; P<0.001), more frequently had CHF (26.2% versus 19.4%; P=0.03), lower IDWG (2.2+/−0.8 versus 2.7+/−0.8 kg; P<0.001), lower normalized UFR (7.1+/−2.5 versus 8.8+/−2.7 mL/kg/h; P<0.001), lower equilibrated normalized protein catabolic rate (enPCR; 0.9+/−0.2 versus 1.0+/−0.2 g/day/kg; P<0.001), lower albumin levels (3.9+/−0.4 versus 4.0+/−0.3 g/dL; P=0.003), lower transferrin saturation (32.4+/−9.0 versus 34.1+/−8.5%; P=0.007) and higher NLR (4.0+/−2.3 versus 3.3+/−1.7; P<0.001).

Figure 22:
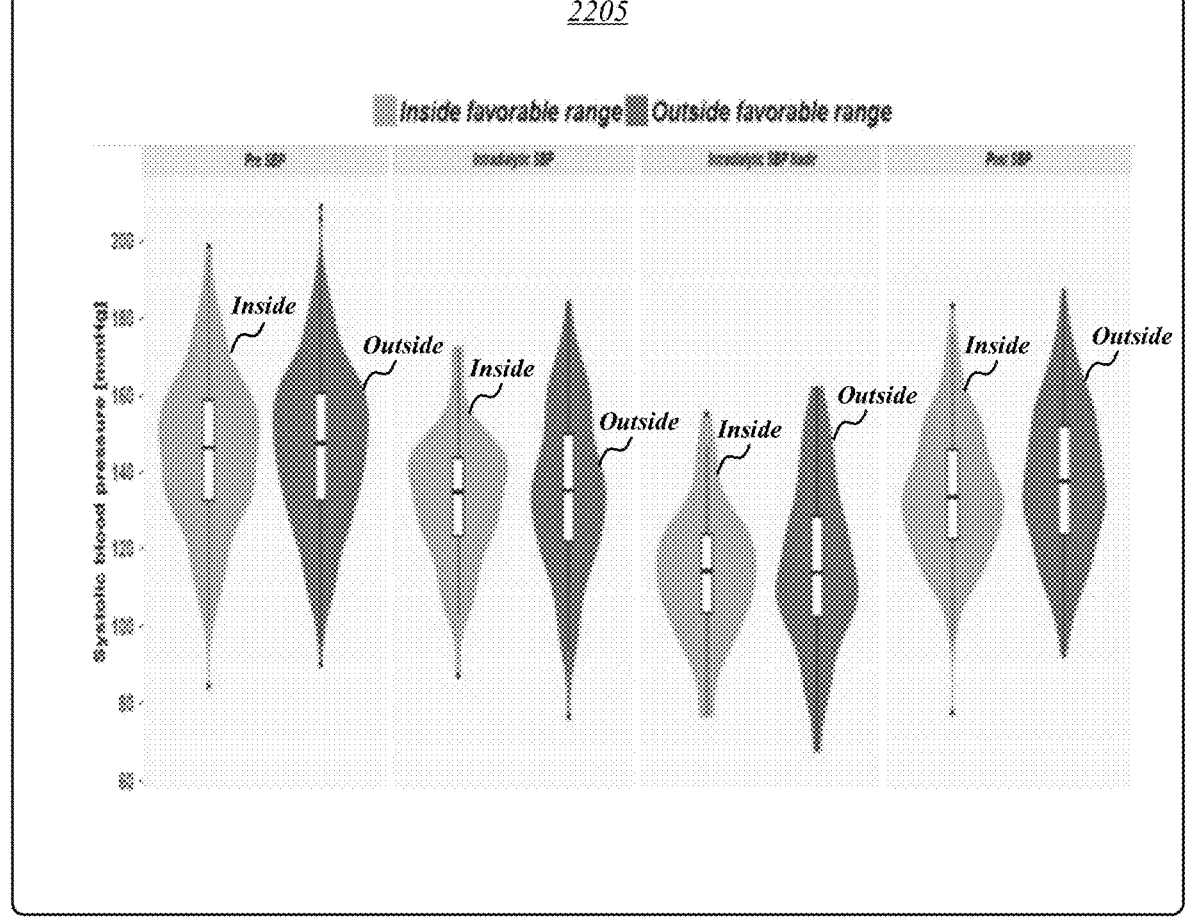

Mean pre-dialysis, post-dialysis, intradialytic and nadir SBPs were 146.3±20.1, 136.6±18.5, 135.3±19.0 and 116.2±19.0 mmHg, respectively. Neither pre-dialysis nor SBP during dialysis differed between patients who did or did not attain a 3-h RBV of 86-92%. Post-dialysis SBP was significantly higher in patients with RBV outside that range (see table 1105 of FIG. 11 and, graph 2205 of FIG. 22).

To explore if the peridialytic SBP behavior was associated with specific RBV levels, the Intradialytic RBV All-Cause Mortality Study stratified patients based on their peridialytic SBP change (post-hemodialysis SBP pre-hemodialysis SBP). Hourly RBV levels were comparable across all groups of peridialytic SBP change (see table 2305 of FIG. 23).

The association between RBV and intradialytic SBP patterns was examined via analyzing those 219 patients with available intradialytic RBV and SPB data. Seventy-six patients (34.7%) were inside the favorable 3-h RBV range and 143 (65.3%) were outside. Neither intradialytic average SBP nor nadir SBP and 10 IDH rate differed between these two groups (see table 2405 of FIG. 24 and table 2505 of FIG. 25). Treatment-level hourly RBVs were comparable between sessions with and without IDH, respectively (see table 2605 of FIG. 26).

Acknowledging the possible influence of fluid administration on RBV, the hourly RBV levels in treatments with documented fluid administration were examined; hourly RBV levels were materially identical (see table 2705 of FIG. 27). Furthermore, neither fluid administration rate nor fluid administration rate in the presence of IDH differed between patients inside or outside the 86-92% 3-h RBV range, respectively (see table 2505 of FIG. 25).

Figure 29:
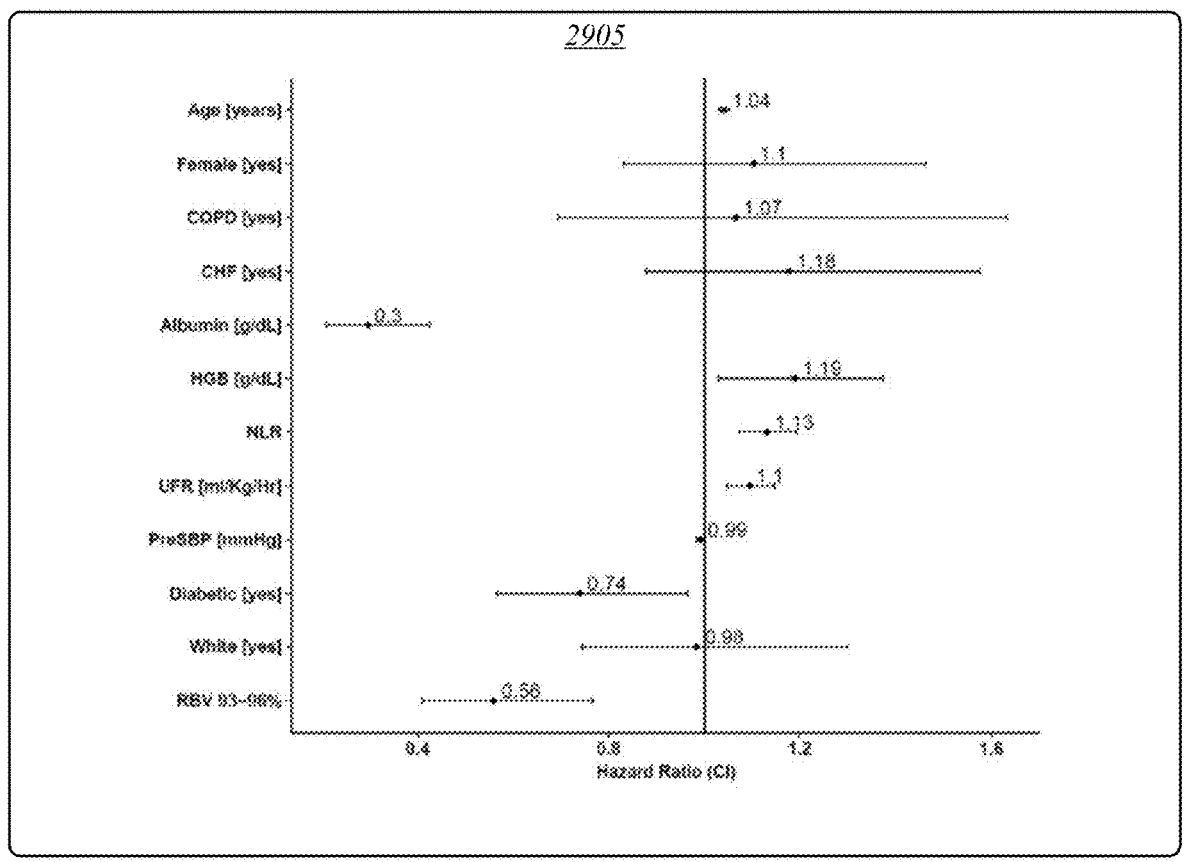

To explore the influence of RBV levels below the favorable RBV ranges on outcomes, HRs for all-cause mortality were computed after excluding patients with RBVs below the lower limits of the hourly favorable RBV ranges. This sensitivity analysis showed materially identical results (see table 2805 of FIG. 28 and graph 2905 of FIG. 29)

To further explore the effect of intradialytic fluid administration on the association between RBV and all-cause mortality, sensitivity analyses were performed on patients with available intradialytic data. Cox proportional hazards models (crude minimally and fully adjusted models) excluding treatments with fluid administration showed essentially identical results.

The Intradialytic RBV All-Cause Mortality Study explored the association between hourly intradialytic RBV levels and all-cause mortality in a large and diverse cohort of chronic HD patients. The main finding is that specific intradialytic RBV ranges are associated with significantly lower all-cause mortality. In addition, in the Intradialytic RBV All-Cause Mortality Study, patients who attained the favorable 3-h RBV range, IDH rates were not increased despite higher UFRs.

Figure 30A:
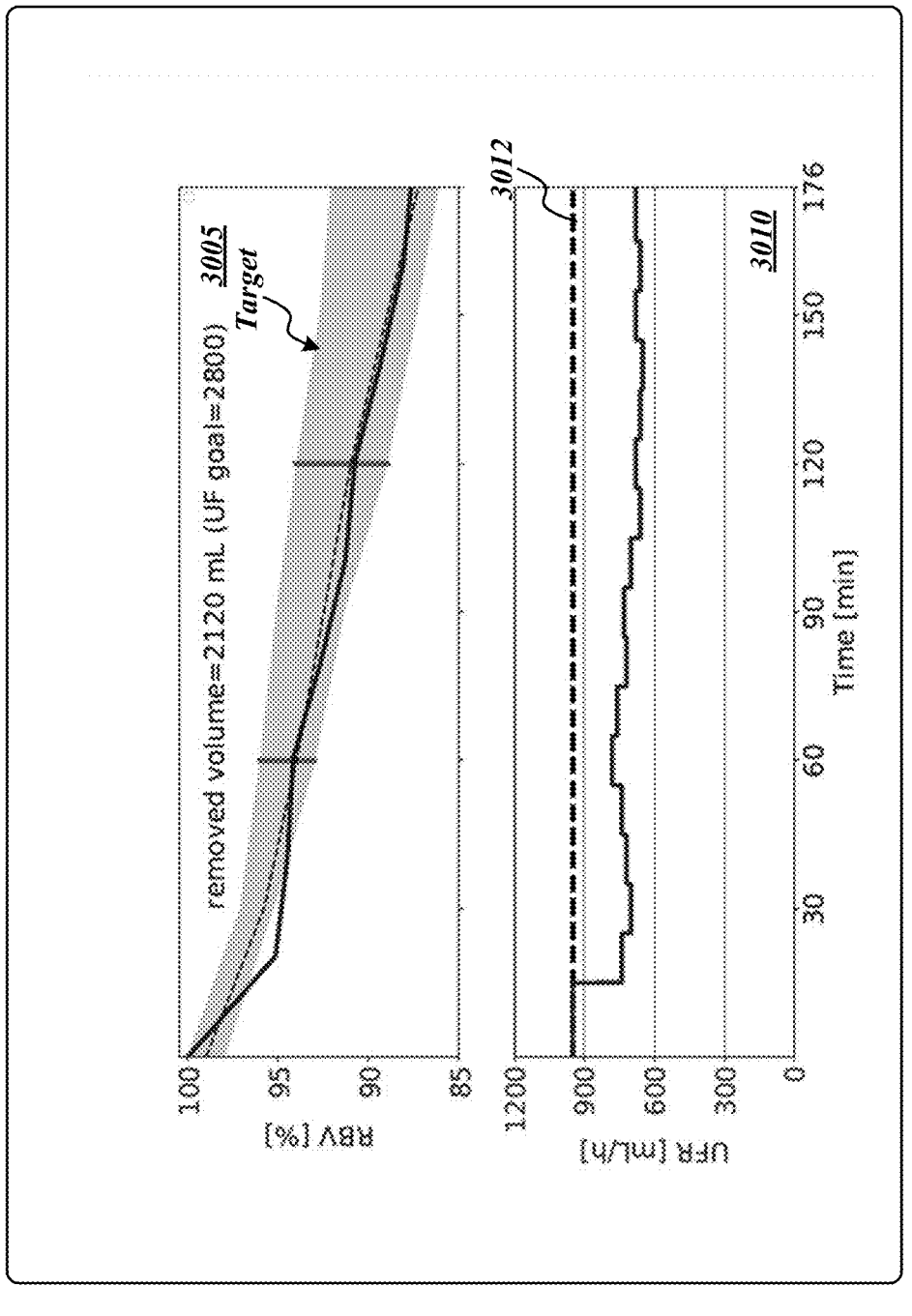
FIGS. 30A-30C depict In-Silico Case Study graphical information.
Figure 30B:
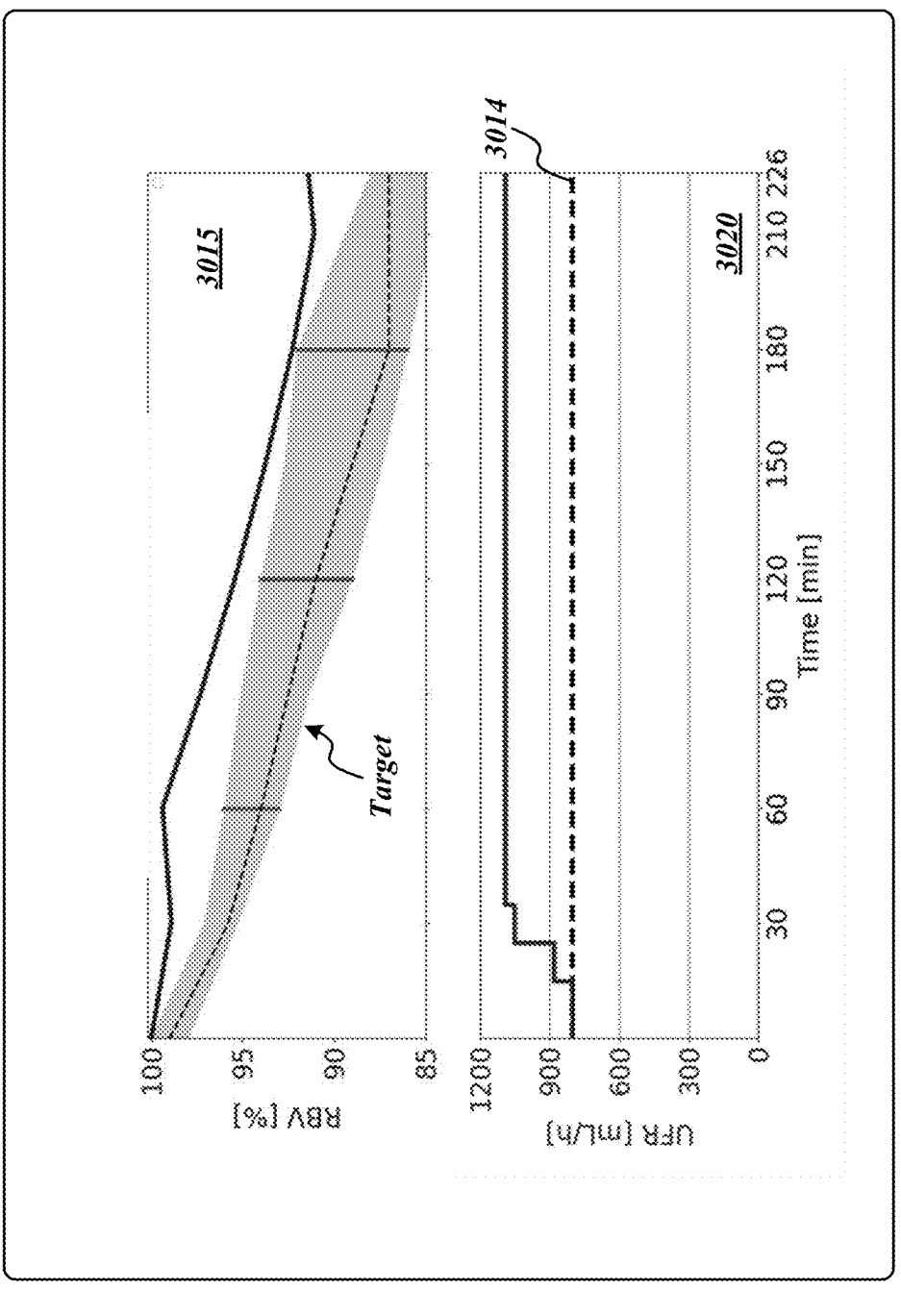
Figure 30C:
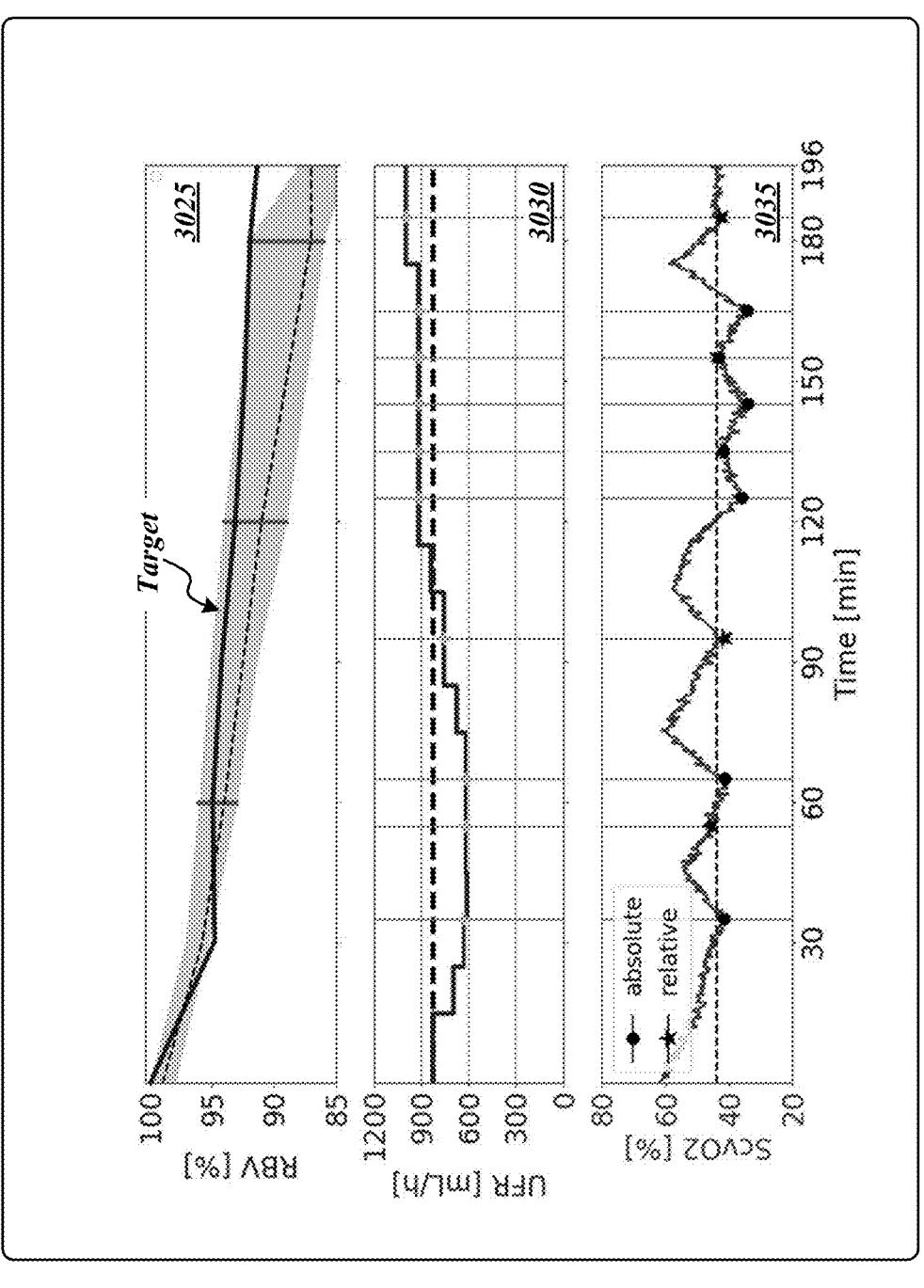
Figure 31A:
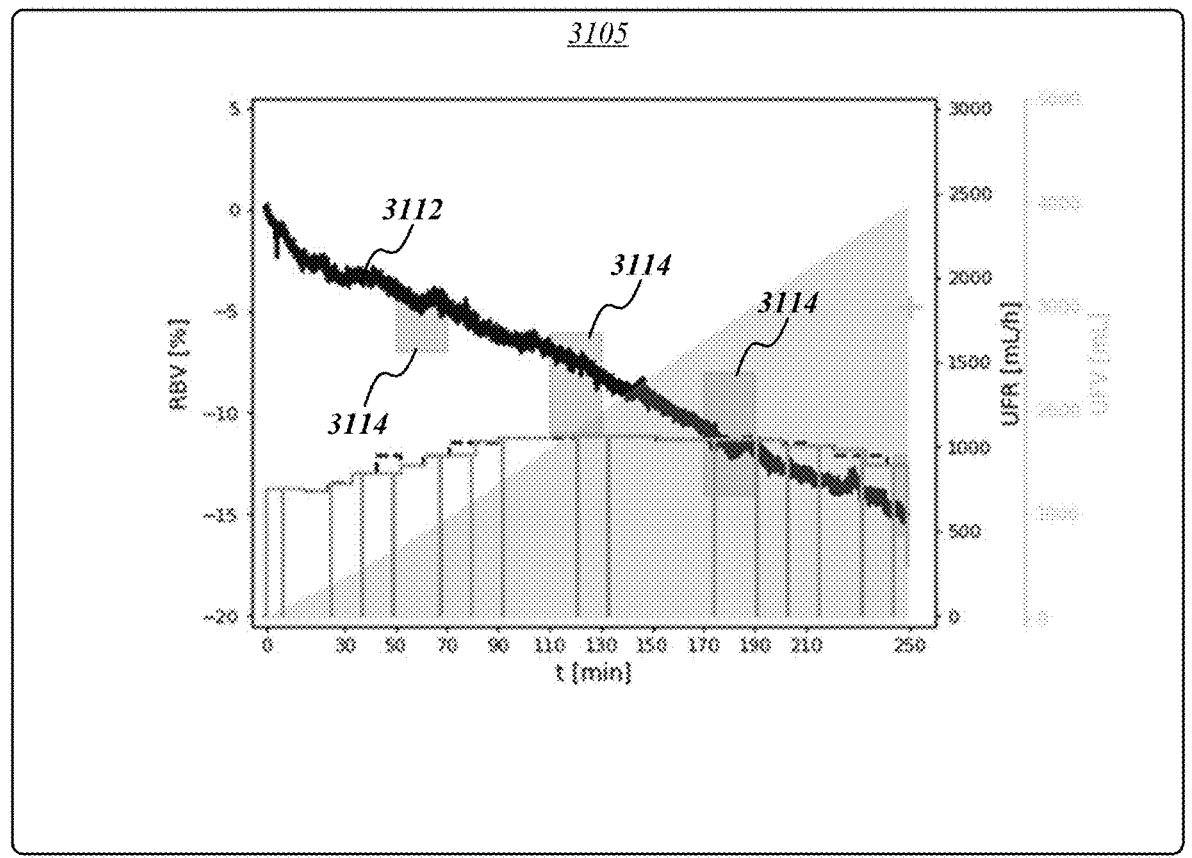
Figure 31B:
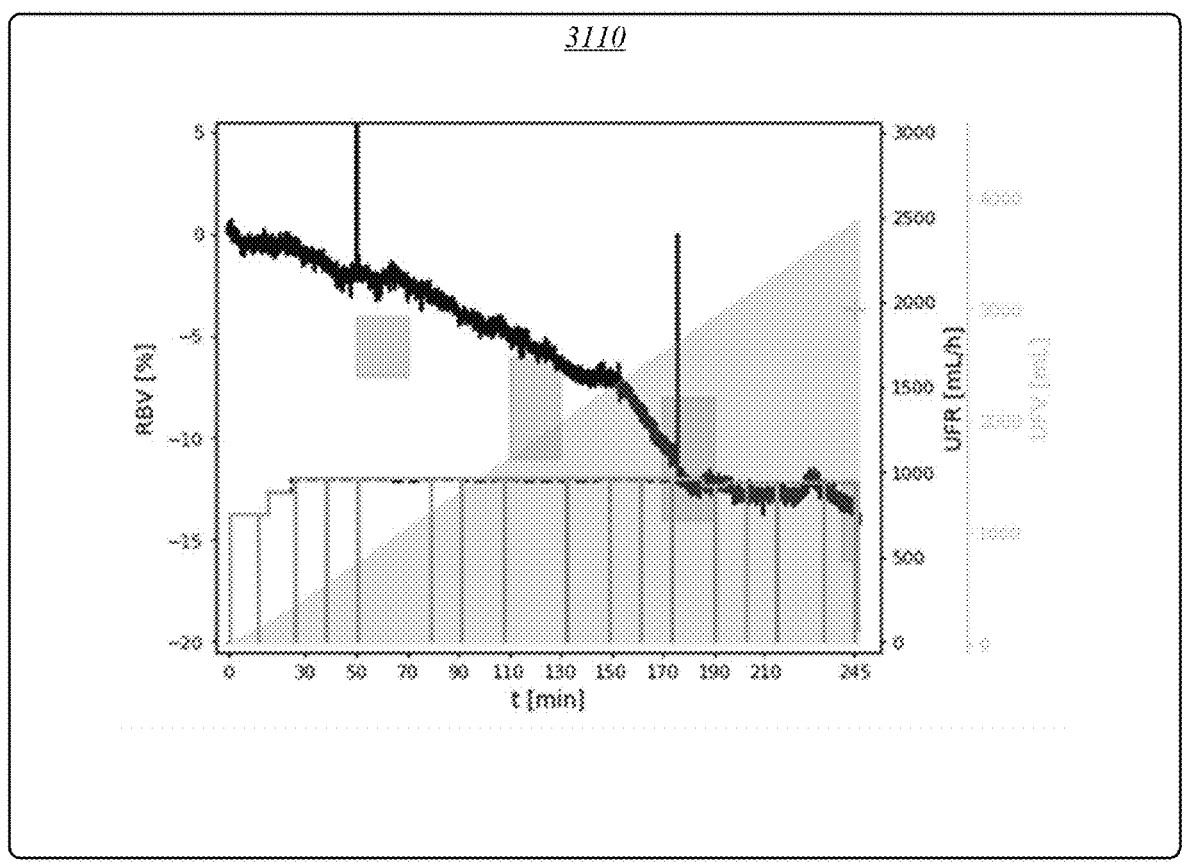
Figure 31C:
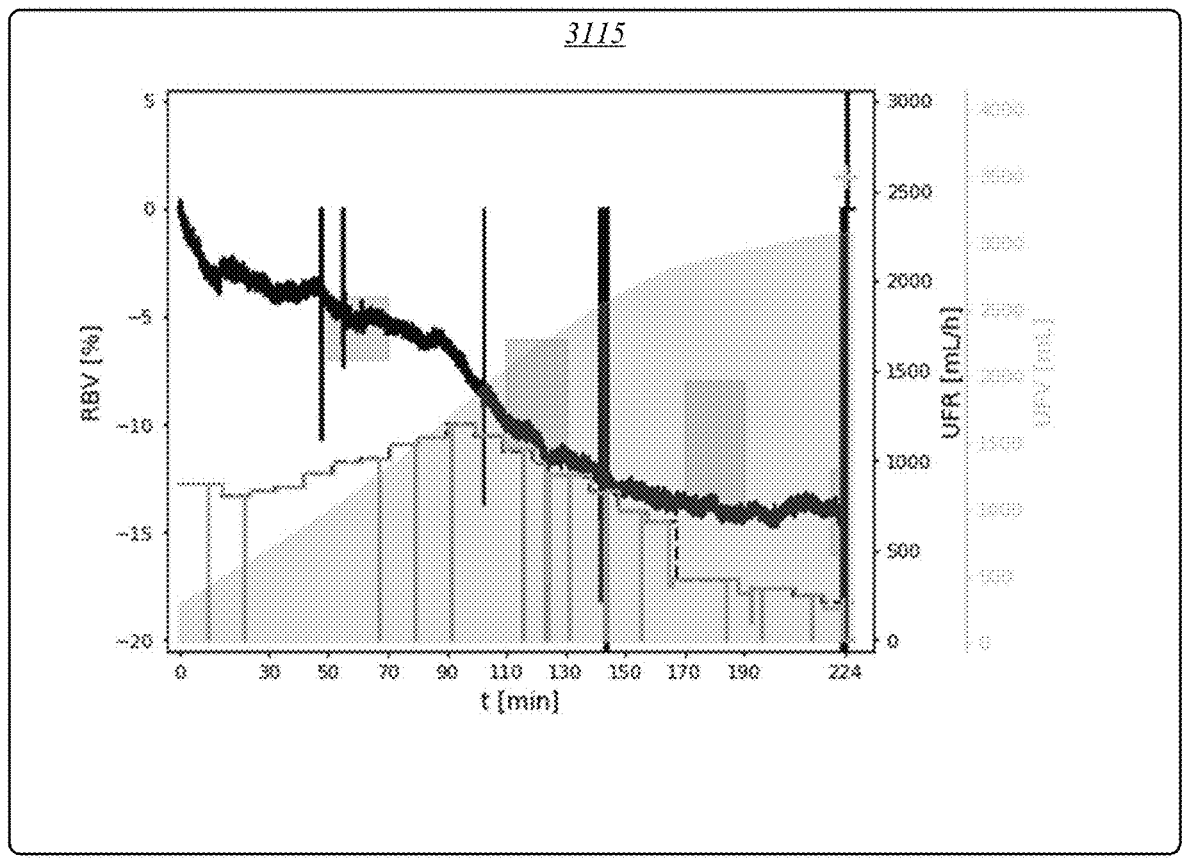
Figure 31D:
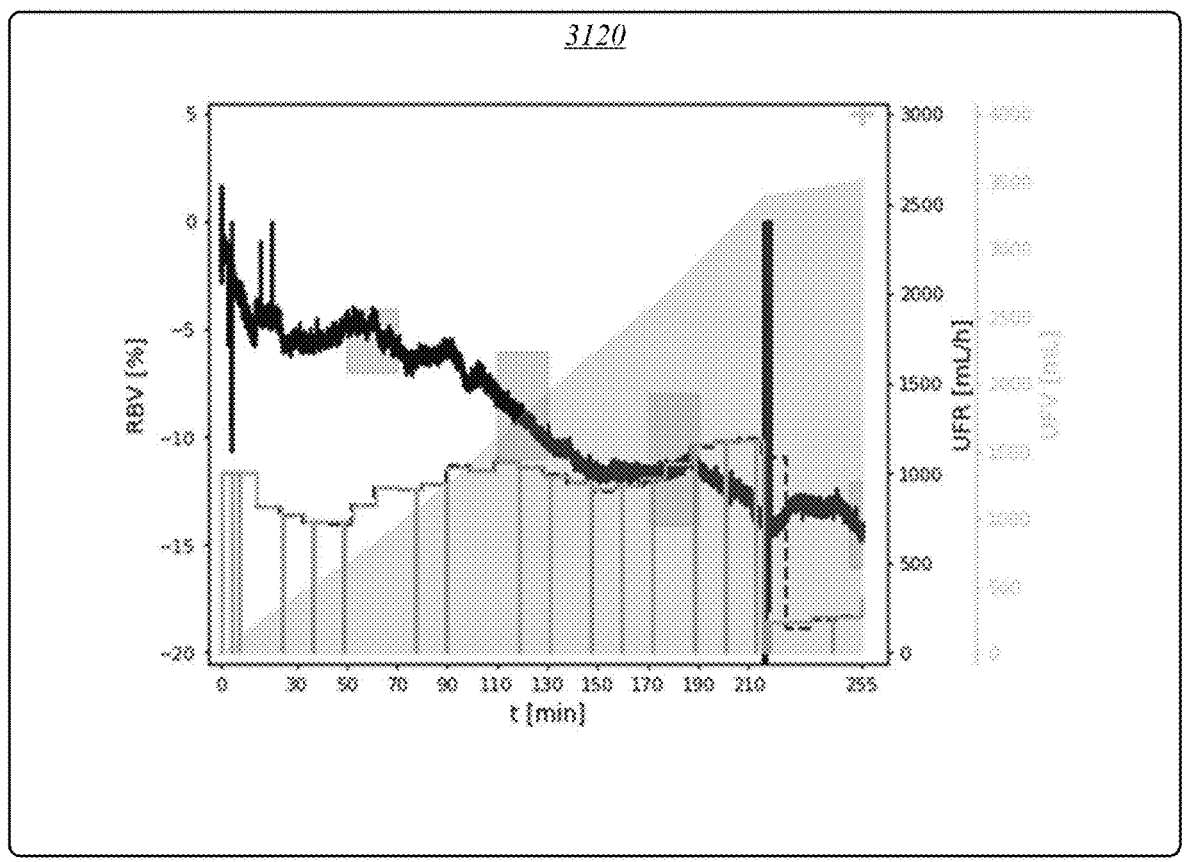

In the Intradialytic RBV All-Cause Mortality Study, about two-thirds of patients attained RBVs above the favorable ranges and <3% of patients were below. Patients with a 3-h RBV above the upper limit of the favorable range had clinical signs of fluid overload, such as higher post-dialysis SBP and a higher prevalence of CHF (see table 1105 of FIG. 11). Patients outside the favorable RBV range were older, had a higher prevalence of CHF, lower enPCR and lower UFRs compared with those patients within the favorable range. In conclusion, the Intradialytic RBV All-Cause Mortality Study indicates that specific intradialytic RBV ranges are associated with all-cause mortality in HD patients.
Case Study 2: In-Silico Case Study The In-Silico Case Study was performed using patient avatars (or "fluid avatars") undergoing simulated dialysis treatment with RBV-based UF control according to some embodiments. FIGS. 30A-30C depict data generated during the In-Silico Case Study. For example, FIG. 30A illustrates graphs 3005 and 3010 depicting RBV vs. time and UFR vs. time, respectively, for a first patient avatar with a prescribed UF goal of 2800 mL and UFR of 960 mL/hour (line 3012 of graph 3010) and actual UF removed of 2120 mL. The first patient avatar had a TBV of −14.6%, a PV of −2.1%, and an ECV/TBW of 22.5/53.5=0.42.

FIG. 30B depicts graphs of RBV vs. time 3015 and UFR vs. time 3020 for a second patient avatar with a prescribed UF goal of 3000 mL and UFR of 800 mL/hour (line 3014 of graph 3020) and actual UF removed of 4000 mL. The second patient avatar had a TBV of −18.7%, a PV of +40.8%, and an ECV/TBW of 22.5/56.8=0.45.

FIG. 30C depicts graphs of RBV vs. time 3025, UFR vs. time 3030, and oxygen saturation vs. time 3035 for a third patient avatar. For the third patient avatar, RBV-based UF control with an oxygen saturation constraint was examined.
Case Study 3: Clinical Pilot Study A Clinical Pilot Study was performed to characterize RBV-based UF control according to some embodiments as a feedback controller designed to guide a patient's RBV curve into predefined target ranges during a hemodialysis treatment. The Clinical Pilot Study was administered as a single arm, prospective, interventional, pilot study in HD patients. The Clinical Pilot Study included 16 patients making a total of 37 study visits. FIGS. 31A-31D depict graphs 3105, 3110, 3115, and 3120 of data generated during the Clinical Pilot Study. For example, referring to FIG. 31A, therein is depicted a graph 3105 showing RBV 3112 managed within a RBV target range 3114. In general, FIGS. 31B and 31C further illustrate the relationship between RBV[%]

measured during the course of a treatment and corresponding adjustments to UFR to return the patient RBV to the "favorability tube."

FIG. 32 illustrates a diagram of an exemplary embodiment of a dialysis system 3200 in accordance with the present disclosure. Dialysis system 3200 may be configured to provide hemodialysis (HD) treatment for a patient 3201. Fluid reservoir 3202 may deliver fresh dialysate to a dialyzer 3204 via tubing 3203, and reservoir 3206 may receive spent dialysate once it has passed through dialyzer 3204 via tubing 3205. A hemodialysis operation may filter particulates and/or contaminates from a patient's blood through a patient external filtration device, for example, a dialyzer 3204. As the dialysate is passed through dialyzer 3204, unfiltered patient blood is also passed into dialyzer 3204 via tubing 3207 and filtered blood is returned to patient 3201 via tubing 3205. Arterial pressure may be monitored via pressure sensor 3210, inflow pressure monitored via sensor 3218, and venous pressure monitored via pressure sensor 3214. An air trap and detector 3216 may ensure that air is not introduced into patient blood as it is filtered and returned to patient 3201. The flow of blood and the flow of dialysate may be controlled via respective pumps, including a blood pump 3212 and a fluid pump 3220. Heparin 3222, a blood thinner, may be used in conjunction with saline 3224 to ensure blood clots do not form or occlude blood flow through the system.

In some embodiments, dialysis system 3200 may include a controller 3250, which may be similar to computing device 110 and/or components thereof (for instance, processor circuitry 420). Controller 3250 may be configured to monitor fluid pressure readings to identify fluctuations indicative of patient parameters, such as heart rate and/or respiration rate. In some embodiments, a patient heart rate and/or respiration rate may be determinable by the fluid pressure in the fluid flow lines and fluid bags. Controller 3250 may also be operatively connected to and/or communicate with additional sensors or sensor systems, devices, and/or the like, although controller 3250 may use any of the data available on the patient's biologic functions or other patient parameters. For example, controller 3250 may send patient data to computing device 110 to perform processes according to some embodiments.

FIG. 33 illustrates an embodiment of an exemplary computing architecture 3300 suitable for implementing various embodiments as previously described. In various embodiments, the computing architecture 3300 may comprise or be implemented as part of an electronic device. In some embodiments, the computing architecture 3300 may be representative, for example, of computing device 3302 and/or components thereof. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 3300. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 3300 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 3300.

As shown in FIG. 33, the computing architecture 3300 comprises a processing unit 3304, a system memory 3306 and a system bus 3308. The processing unit 3304 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 3304.

The system bus 3308 provides an interface for system components including, but not limited to, the system memory 3306 to the processing unit 3304. The system bus 3308 can be any of several types of bus structure that may further interconnect to a memory bus (with or without a memory controller), a peripheral bus, and a local bus using any of a variety of commercially available bus architectures. Interface adapters may connect to the system bus 3308 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 3306 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 33, the system memory 3306 can include non-volatile memory 3310 and/or volatile memory 3312. A basic input/output system (BIOS) can be stored in the non-volatile memory 3310.

The computer 3302 may include various types of computer-readable storage media in the form of one or more lower speed memory units, including an internal (or external) hard disk drive (HDD) 3314, a magnetic floppy disk drive (FDD) 3316 to read from or write to a removable magnetic disk 3318, and an optical disk drive 3320 to read from or write to a removable optical disk 3322 (e.g., a CD-ROM or DVD). The HDD 3314, FDD 3316 and optical disk drive 3320 can be connected to the system bus 3308 by a HDD interface 3324, an FDD interface 3326 and an optical drive interface 3329, respectively. The HDD interface 3324 for external drive implementations can include at least one or both of Universal Serial Bus (USB) and IEEE 1384 interface technologies.

The drives and associated computer-readable media provide volatile and/or nonvolatile storage of data, data structures, computer-executable instructions, and so forth. For example, a number of program modules can be stored in the drives and memory units 3310, 3312, including an operating system 3330, one or more application programs 3332, other program modules 3334, and program data 3336. In one embodiment, the one or more application programs 3332, other program modules 3334, and program data 3336 can include, for example, the various applications and/or components of computing device 110.

A user can enter commands and information into the computer 3302 through one or more wire/wireless input devices, for example, a keyboard 3338 and a pointing device, such as a mouse 3340. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 3304 through an input device interface 3342 that is coupled to the system bus 3308, but can be connected by other interfaces such as a parallel port, IEEE 994 serial port, a game port, a USB port, an IR interface, and so forth.

A monitor 3344 or other type of display device is also connected to the system bus 3308 via an interface, such as a video adaptor 3346. The monitor 3344 may be internal or external to the computer 3302. In addition to the monitor 3344, a computer typically includes other peripheral output devices, such as speakers, printers, and so forth.

The computer 3302 may operate in a networked environment using logical connections via wire and/or wireless communications to one or more remote computers, such as a remote computer 3349. The remote computer 3349 can be a workstation, a server computer, a router, a personal computer, portable computer, microprocessor-based entertainment appliance, a peer device or other common network node, and typically includes many or all of the elements described relative to the computer 3302, although, for purposes of brevity, only a memory/storage device 3350 is illustrated. The logical connections depicted include wire/wireless connectivity to a local area network (LAN) 3352 and/or larger networks, for example, a wide area network (WAN) 3354. Such LAN and WAN networking environments are commonplace in offices and companies, and facilitate enterprise-wide computer networks, such as intranets, all of which may connect to a global communications network, for example, the Internet.

When used in a LAN networking environment, the computer 3302 is connected to the LAN 3352 through a wire and/or wireless communication network interface or adaptor 3356. The adaptor 3356 can facilitate wire and/or wireless communications to the LAN 3352, which may also include a wireless access point disposed thereon for communicating with the wireless functionality of the adaptor 3356.

When used in a WAN networking environment, the computer 3302 can include a modem 3358, or is connected to a communications server on the WAN 3354, or has other means for establishing communications over the WAN 3354, such as by way of the Internet. The modem 3359, which can be internal or external and a wire and/or wireless device, connects to the system bus 3308 via the input device interface 3342. In a networked environment, program modules depicted relative to the computer 3302, or portions thereof, can be stored in the remote memory/storage device 3350. It will be appreciated that the network connections shown are exemplary and other means of establishing a communications link between the computers can be used.

The computer 3302 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method comprising:
   performing a hemodialysis (HD) treatment on a patient using a dialysis machine;
   determining a target ultrafiltration rate (UFR) using a computing device operably coupled to the dialysis machine, the computing device comprising a memory storing instructions and a processor, responsive to executing the instructions, operative to determine the target UFR via:
      determining RBV target information for the patient based on population-based dialysis data of real patient outcomes of a patient population sharing at least one characteristic of the patient, the RBV target information comprising desired RBV target ranges for the patient during the dialysis process;
      measuring relative blood volume (RBV) values of the patient during the dialysis treatment;
      comparing the RBV values to the RBV target information;
      determining the target UFR to maintain future RBV values of the patient during the dialysis treatment within the RBV target ranges; and
      communicating the target UFR to the dialysis machine; and
   controlling a UFR of the dialysis machine to correspond to the target UFR during the HD treatment.

2. The method of claim 1, comprising determining the UFR based on at least one constraint, the at least one constraint comprising at least one of: a maximum UF rate (UFR) change, oxygen saturation, blood pressure, or IDH prediction.

3. The method of claim 2, the maximum UFR rate change determined based on one of an elapsed time of the dialysis process or whether the RBV value is within the favorability tube or outside of the favorability tube.

4. The method of claim 1, further comprising determining the RBV target information based on Cox proportional hazard models with spline terms on the population-based dialysis data of a patient population sharing the at least one characteristic.

5. The method of claim 1, wherein the population-based dialysis data includes RBV ranges for improved patient outcomes based on factors including one or more of hazard ratios, morbidity values, mortality values, or complication rates.

6. The method of claim 1, wherein the patient population includes a patient population of a clinical trial.

7. The method of claim 1, wherein the characteristic of the patient includes one or more of age, gender, disease state, fluid removal volume, or complications.

8. The method of claim 1, wherein the desired RBV target ranges are determined based on one or more optimal target RBV curves.

9. The method of claim 1, wherein measuring the RBV values of the patient incudes obtaining the RBV values of the patient using a patient monitoring device.

10. The method of claim 1, wherein the RBV values of the patient are determined based on patient hematocrit values.

11. The method of claim 1, wherein controlling the UFR of the dialysis machine includes controlling a UF pump of the dialysis machine.

12. The method of claim 1, wherein controlling the UFR of the dialysis machine includes control circuitry of a UF pump of the dialysis machine:

receiving the target UFR; and adjusting operation of the UF pump to achieve the target UFR.

* * * * *